US005908969A

United States Patent [19]

Prusiner et al.

[11] Patent Number: 5,908,969
[45] Date of Patent: *Jun. 1, 1999

[54] METHOD OF DETECTING PRIONS IN A SAMPLE AND TRANSGENIC ANIMAL USED FOR SAME

[75] Inventors: Stanley B. Prusiner; Michael R. Scott; Glenn Telling, all of San Francisco, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/521,992

[22] Filed: Aug. 31, 1995

Related U.S. Application Data

[63] Continuation-in-part of application No. 08/509,261, Jul. 31, 1995, Pat. No. 5,763,740, which is a continuation-in-part of application No. 08/242,188, May 13, 1994, Pat. No. 5,565,186.

[51] Int. Cl.$^6$ ................................................ C12P 21/00
[52] U.S. Cl. .................................. 800/4; 800/18
[58] Field of Search .................... 800/2, 4, 18; 530/350, 530/69.1; 435/172.3

[56] References Cited

U.S. PATENT DOCUMENTS 5,237,056   8/1993   Fischbach .............................. 536/23.5

FOREIGN PATENT DOCUMENTS

WO 93/10227   5/1995   WIPO.

OTHER PUBLICATIONS

Scott et al., 1992, "Chimeric prion protein expression in cultured cells and transgenic mice", Protein Science 1:986–997, 1992.

Basler et al., "Scrapie and Cellular PrP Isoforms Are Encoded by the Same Chromosomal Gene," Cell, (1986) 46:417–28.

Bolton et al., "Identification of a Protein That Purifies with the Scrapie Prion," Science (1982) 218: 1309–11.

Brown, et al., "Friendly Fire' in Medicine: Hormones, Homografts, and Cruetzfeldt–Jakob Disease," Lancet (1992) 340: 24–27.

Buchanan et al., "Mortality, Neoplasia, and Creutzfeld–Jakob Disease in Patients Treated with Human Pituitary Growth Hormone in the United Kingdom", BMJ (1991) 302:824–828.

Bueler et al., "Mice Devoid of PrP are Resistant to Scrapie," Cell (1993) 73:1339–1347.

Bueler et al., "Normal Development and Behavior of Mice Lacking the Neuronal Cell–surface PrP Protein," Nature (1992) 356:577–582.

Carlson et al., "Linkage of Protein and Scrapie Incubation Time Genes," Cell (1986) 46:503–511.

Cochius et al, "Creutzfeldt–Jakob Disease in a Recipient of Human Pituitary–Derived Gonadotrophin: A Second Case," J. Neurol. Neurosurg. Psychiatry (1992) 55:1094–1095.

Cochius et al., "Creutzfeldt–Jakob Disease in a Recipient of Human Pituitary–Derived Gonadotrophin," Aust. N.Z. J. Med. (1990) 20:592–593.

Collinge et al, "Genetic Predisposition to Latrogenic Creutzfeldt–Jakob Disease," Lancet (1991) 337:1441–1442.

Gabriel et al., "Molecular Cloning of a Candidate Chicken Prion Protein," Proc. Natl. Acad. Sci. USA (1992) 89:9097–9101.

Gajdusek, D.C., "Unconventional Viruses and the Origin and Disappearance of Kuru," Science (1977) 197:943–960.

Gibbs, Jr. et al., "Creutzfeldt–Jakob Disease Infectivity of Growth Hormone Derived from Human Pituitary Glands," N.Engl. J. Med. (1993) 328:358–359.

Goldfarb et al, "Fatal Familial Insomnia and Familial Creutzfeldt–Jakob Disease: Disease Phenotype Determined by a DNA Polymorphism," Science (1992) 258:806–808.

Goldmann et al., "Two Alleles of a Neural Protein Gene Linked to Scrapie in Sheep," Proc. Natl. Acad. Sci. USA (1990) 87:2476–2480.

Goldmann et al., "Different Forms of the Bovine PrP Gene Have Five or Six Copies of a Short, G–C Rich Element within the protein–coding Exon," J. Gen. Virol. (1991) 72:201–204.

Harris et al., "A Prion–like Protein from Chicken Brain Copurifies with an Acetylcholine Receptor–Inducing Activity," Proc. Natl. Acad. Sci. USA (1991) 88:7664–7668.

(List continued on next page.)

*Primary Examiner*—Brian R. Stanton
*Assistant Examiner*—Anne Marie S. Beckerleg
*Attorney, Agent, or Firm*—Karl Bozicevic; Bozicevic & Reed LLP

[57] ABSTRACT

The invention includes an artificial PrP gene, a transgenic animal containing a PrP gene of another animal or the artificial PrP gene, a hybrid non-human mammal with an ablated endogenous prion protein gene and exogenous prion protein gene, assay methodology which uses the animals to detect pathogenic prions in a sample or diagnose a cause of death and standardized prion preparation used in the assay. The genome of a host animal (such as a mouse), is manipulated so that the animal is rendered susceptible to infection with prions which normally would infect only a genetically diverse test animal (such as human, cow or sheep). Pathogenic prions in a sample can be detected by injecting the sample to be tested into a mammal of the invention which has been genetically manipulated so as to be susceptible to infection from prions in the sample. Mammals which are not inoculated with the sample and others inoculated with a standardized prion preparation of the invention are used as controls in the assay to detect prions in samples which cause diseases. For example, Creutzfeldt Jakob Disease (CJD) is a fatal neurodegenerative disease of humans caused by prions. The mammals disclosed herein develop the adverse effects of such prions in a relatively short time after being inoculated with human prions.

7 Claims, 1 Drawing Sheet

OTHER PUBLICATIONS

Healy et al., "Creutzfeldt–Jakob Disease After Pituitary Gonadotrophins: The Prion is the Problem," *BMJ* (1993) 307:517–518.

Hecker et al., "Replication of Distinct Scrapie Prion Isolates is Region Specific in Brains of Transgenic Mice and Hamsters," *Genes Dev.* (1992) 6:1213–1228.

Hsaio et al., "Linkage of a Prion Protein Missense Variant to Gerstmann–Straussler Syndrome," *Nature* (1989) 383:342–345.

Hsaio et al., "A Prion Protein Variant in a Family with the Telencephalic Form of Gerstmann–Strussler–Scheinker Syndrome," *Neurology* (1991) 41:681–684.

Hsaio et al., "Inherited Human Prion Diseases," *Neurology* (1990) 40:1820–1827.

Koch et al., "Creutzfeldt–Jakob Disease in a Young Adult with Idiopathic Hypopituitarism," *N. Engl. J. Med.* (1985) 313:731–733.

Kretzschmar et al., "Molecular Cloning of a Human Prion Protein cDNA," *DNA* (1986) 5:315–324.

Kretzschmar et al., "Molecular Cloning of a Mink Prion Protein Gene," *J.Gen.Virol.* (1992) 73:2757–2761.

Lasmezas et al.,"Recombinant Human Growth Hormone and Insulin–Like Growth Factor I Induce PRP Gene Expression in PC12 Cell," *Biochem. Biophys. Res.Commun.* (1993) 196:1163–1169.

Locht et al.,"Molecular Cloning and Complete Sequence of Prion Protein cDNA from Mouse Brain Infected with the Scrapie Agent," *Proc. Natl. Acad. Sci USA* (1986) 83:6372–6376.

Manuelidis et al., "Serial Propagation of Creutzfeldt–Jakob Disease in Guinea Pigs," *Proc. Natl. Acad. Sci. USA* (1976) 73:223–227.

Manuelidis et al., "Interspecies Transmission of Creutzfeldt–Jakob Disease to Syrian Hamsters with Reference to Clinical Syndromes and Strain of Agent," *Proc. Natl. Acad. Sci. USA* (1978) 75:3432–3436.

McKinley et al, "A Protease–Resistant Protein is a Structural Component of the Scrapie Prion," *Cell* (1983) 35:57–62.

Medori et al., "Fatal Familial Insomnia, a Prion Disease with a Mutation at Codon 178 of the Prion Protein Gene," *N. Engl.J. Med.* (1992) 326:444–449.

Nisbet et al.,"Creutzfeldt–Jakob Disease in a Second Patient Who Received a Cadeveric Dura mater Graft," *J.Am. Med.Assoc.* (1989) 261:1118.

Patel, "France Reels at Latest Medical Scandal," *New Scientist*, Jul. 31, 1993, p. 4.

Patel, "Placenta Donors to be Screened for Brain Disease," *New Scientist*, Nov. 20, 1993, p. 10.

Prusiner et al., "Ablation of the Prion Protein (PrP) Gene in Mice Prevents Scrapie and Facilitates Production of Anti–Prp Antibodies," *Proc. Natl. Acad. Sci. USA* (1993) 90:10608–10612.

Prusiner et al., "Prion Diseases and Neurodegeneration," *Ann.Rev.Neurosci.* (1994) 17:311–339.

Prusiner et al., "Transgenic Studies Implicate Interactions Between Homologous PrP Isoforms in Scrapie Prion Replication," *Cell* (1990) 63:673–686.

Prusiner et al., "Molecular Biology of Prion Diseases," *Science* (1991) 252:1515–1522.

Prusiner et al, "Further Purification and Characterization of Scrapie Prions," *Biochemistry* (1982) 21:6942–50.

Raeber et al., "Attempts to Convert the Cellular Prion Protein into the Scrapie Isoform in Cell–Free Systems," *J. Virol.* (1992) 66:6155–6163.

Scott et al, "Propagation of Prions with Artificial Properties in Transgenic Mice Expressing Chimeric PrP Genes," *Cell* (1993) 73:979–988.

Stahl et al., "Glycosylinositol Phospholipid Anchors of the Scrapie and Cellular Prion Proteins Contain Sialic Acid," *Biochemistry* (1992) 31:5043–5053.

Taraboulos et al., "Regional Mapping of Prion Proteins in Brain," *Proc. Natl. Acad. Sci. USA* (1992) 89:7620–7624.

Tateishi et al.,"Transmission of Chronic Spongiform Encephalopathy with Kuru Plaques from Humans to Small Rodents," *Ann. Neurol.* (1979) 5:581–584.

Thadani et al., "Creutzfeldt–Jakob Disease Probably Acquired From a Cadaveric Dura Mater Graft," *J. Neurosurg.* (1988) 69:766–769.

Westaway et al., Homozygosity for Prion Protein Alleles Encoding Glutamine–171 Renders Sheep Susceptible to Natural Scrapie,: *Genes. Dev.* (1994) 8:959–969.

Westaway et al., "Degeneration of Skeletal Muscle, Peripheral Nerves, and the Central Nervous System in Transgenic Mice Overexpressing Wild–Type Prion Proteins," *Cell* (1994) 76:117–129.

Willison et al., "Creutzfeldt–Jakob Disease Following Cadaveric Dura Mater Graft," *Neurosurg. Psychiatric* (1991) 54:940.

5,908,969

METHOD OF DETECTING PRIONS IN A SAMPLE AND TRANSGENIC ANIMAL USED FOR SAME

CROSS-REFERENCE

This application is a continuation-in-part of our earlier filed application Ser. No. 08/509,261, filed Jul. 31, 1995, now U.S. Pat. No. 5,763,740 which is a continuation-in-part of our earlier filed application Ser. No. 08/242,188, filed May 13, 1994, now U.S. Pat. No. 5,565,186, both of which applications are incorporated herein by reference in their entirety and to which applications we claim priority under 35 USC §120.

GOVERNMENT RIGHTS

The United States Government may have certain rights in this application pursuant to Grant Nos. NS14069, AG02132, NS22786, AG08967 and AG10770 awarded by the National Institutes of Health.

FIELD OF THE INVENTION

This invention relates generally to chimeric genes, methods of assaying and to transgenic animals used in such assays. More specifically, this invention relates to artificial and chimeric PrP genes, assaying samples for pathogenic prions, standardized prion preparations used in such assays and to transgenic mice and hybrid transgenic mice which can be infected which prions which generally only infect a genetically diverse species.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") [Bolton et al., *Science* 218:1309–11 (1982); Prusiner et al., *Biochemistry* 21:6942–50 (1982); McKinley et al., *Cell* 35:57–62 (1983)]. Complete prion protein-encoding genes have since been cloned, sequenced and expressed in transgenic animals. $PrP^C$ is encoded by a single-copy host gene [Basler et al., *Cell* 46:417–28 (1986)] and is normally found at the outer surface of neurons. A leading hypothesis is that prion diseases result from conversion of $PrP^C$ into a modified form called $PrP^{Sc}$. However, the actual biological or physiological function of $PrP^C$ is not known.

It appears that the scrapie isoform of the prion protein ($PrP^{Sc}$) is necessary for both the transmission and pathogenesis of the transmissible neurodegenerative diseases of animals and humans. See Prusiner, S. B., "Molecular biology of prion disease," *Science* 252:1515–1522 (1991). The most common prion diseases of animals are scrapie of sheep and goats and bovine spongiform encephalopathy (BSE) of cattle [Wilesmith, J. and Wells, *Microbiol. Immunol.* 172:21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D. C., *Science* 197:943–960 (1977); Medori et al., *N. Engl. J. Med.* 326:444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., *Neurology* 40:1820–1827 (1990); Goldfarb et al., *Science* 258:806–808 (1992); Kitamoto et al., *Proc. R. Soc. Lond.* (In press) (1994)]. Iatrogenic CJD has been caused by human growth hormone derived from cadaveric pituitaries as well as dura mater grafts [Brown et al., *Lancet* 340:24–27 (1992)]. Despite numerous attempts to link CJD to an infectious source such as the consumption of scrapie infected sheep meat, none has been identified to date [Harries-Jones et al., *J. Neurol. Neurosurg. Psychiatry* 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., *Slow Transmissible Diseases of the Nervous System*, Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into non-human primates and that the animals be observed for disease that was predicted to occur after a prolonged incubation period [Hadlow, W. J., *Lancet* 2:289–290 (1959)]. Seven years later, Gajdusek, Gibbs and Alpers demonstrated the transmissibility of kuru to chimpanzees after incubation periods ranging form 18 to 21 months [Gajdusek et al., *Nature* 209:794–796 (1966)]. The similarity of the neuropathology of kuru with that of CJD [Klatzo et al., *Lab Invest.* 8:799–847 (1959)] prompted similar experiments with chimpanzees and transmissions of disease were reported in 1968 [Gibbs, Jr. et al., *Science* 161:388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using non-human primates, some cases of human prion disease have been transmitted to rodents but apparently with less regularity [Gibbs, Jr. et al., *Slow Transmissible Diseases of the Nervous System*, Vol. 2, S. B. Prusiner and W. J. Hadlow, eds. (New York: Academic Press), pp. 87–110 (1979); Tateishi et al., *Prion Diseases of Humans and Animals*, Prusiner et al., eds. (London: Ellis Horwood), pp. 129–134 (1992)].

The infrequent transmission of human prion disease to rodents has been cited as an example of the "species barrier" first described by Pattison in his studies of passaging the scrapie agent between sheep and rodents [Pattison, I. H., *NINDB Monograph* 2, D. C. Gajdusek, C. J. Gibbs Jr. and M. P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott et al., *Cell* 59:847–857 (1989)]. SHaPrP differs from MoPrP at 16 positions out of 254 amino acid residues [Basler et al., *Cell* 46:417–428 (1986); Locht et al., *Proc. Natl. Acad. Sci. USA* 83:6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. The seriousness of the health risk resulting from the lack of such a test is exemplified below.

More than 45 young adults previously treated with HGH derived from human pituitaries have developed CJD [Koch et al., *N. Engl. J. Med.* 313:731–733 (1985); Brown et al., *Lancet* 340:24–27 (1992); Fradkin et al., *JAMA* 265:880–884 (1991); Buchanan et al., *Br. Med. J.* 302:824–828 (1991)]. Fortunately, recombinant HGH is now used, although the seemingly remote possibility has been raised that increased expression of wtPrP$^C$ stimulated by high HGH might induce prion disease [Lasmezas et al., *Biochem. Biophys. Res. Commun.* 196:1163–1169 (1993)]. That the HGH prepared from pituitaries was contaminated with prions is supported by the transmission of prion disease to a monkey 66 months after inoculation with a suspect lot of HGH [Gibbs, Jr. et al., *N. Engl. J. Med.* 328:358–359 (1993)]. The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone [Healy et al., *Br. J. Med.* 307:517–518 (1993); Cochius et al., *Aust. N.Z. J. Med.* 20:592–593 (1990); Cochius et al., *J. Neurol. Neurosurg. Psychiatry* 55:1094–1095 (1992)] as well as at least 11 patients receiving dura mater grafts [Nisbet et al., *J. Am. Med. Assoc.* 261:1118 (1989); Thadani et al., *J. Neurosurg.* 69:766–769 (1988); Willison et al., *J. Neurosurg. Psychiatric* 54:940 (1991); Brown et al., *Lancet* 340:24–27 (1992)]. These cases of iatrogenic CJD underscore the need for screening pharmaceuticals that might possibly be contaminated with prions.

Recently, two doctors in France were charged with involuntary manslaughter of a child who had been treated with growth hormones extracted from corpses. The child developed Creutzfeldt-Jakob Disease. (See *New Scientist*, Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist*, Nov. 20, 1993, page 10.) In view of such, there clearly is a need for a convenient, cost-effective assay for testing sample materials for the presence of prions which cause CJD. The present invention offers such an assay.

SUMMARY OF THE INVENTION

The invention includes an artificial PrP gene, a transgenic animal containing the artificial gene or elevated expression of a PrP gene from a genetically diverse animal, hybrid transgenic animals which are the offspring of different transgenic animals with each other or with a transgenic animal that has an ablated endogenous prion protein gene, a standardized prion preparation and assay methodology which uses the preparation and genetically altered animals to detect pathogenic prions in a sample. The artificial gene includes a sequence such that when it is inserted into the genome of an animal (such as a mouse), the animal is rendered susceptible to infection with prions which normally would infect only a specific species of genetically diverse animal (such as a human, cow, sheep, pig, chicken, cat or dog). The artificial PrP gene may be comprised partially or completely of an artificial polynucleotide sequence, i.e. codon sequences not present in any native PrP gene sequence. Alternatively, the artificial gene may be comprised of the codon sequence of a host animal with one or more codon substitutions being made wherein the substitutions are preferably corresponding PrP gene codons from a genetically diverse animal, meaning that PrP gene differs from the PrP gene of the host animal by 20 or more codons. Transgenic animals containing elevated levels of expression of the PrP gene which can be obtained for example, by over expression of the gene with an enhanced promoter and/or with high copy numbers of the natural PrP gene of a genetically diverse animal are also disclosed. Hybrid transgenic animals include animals resulting from a cross between two transgenic animals and in particular a cross between a transgenic animal containing the entire prion protein gene of a genetically diverse animal (e.g., a mouse containing a human prion protein gene) and an animal with its endogenous prion protein gene disrupted (e.g., a mouse with an ablated prion protein gene). Hybrids also specifically include crossing a transgenic animal having a chimeric prion protein gene with an animal with its endogenous prion protein gene ablated.

Genetics constructs and methodologies of the invention are used to create animals which due to their genetic make up will develop disease from inoculation with prions which would generally only infect a genetically diverse animal, e.g., a mouse of the invention will consistently become infected with prions which generally will only infect a human and symptoms of the infection will become apparent in a short period e.g., 350 days or less. The animals of the invention are used in assays to test samples of any given material to determine if the material includes prions which would infect another animal (such as a human) if the material were ingested or injected. Standardized prion preparations of the invention are used to inoculate animals of the invention to create controls when carrying out an assay of the invention. The standardized prion preparation will always contain prions which will infect a genetically modified animal of the invention which animal will develop clinical signs of CNS dysfunction within a set period of time.

In one preferred example the mouse genome includes a chimeric PrP gene which gene includes a portion of a gene of the animal (e.g. human) in danger of infection from prions in the sample. For example, Creutzfeldt Jakob Disease (CJD) is a fatal neurodegenerative disease of humans caused by prions. Preferred transgenic (Tg) mice disclosed herein express a chimeric prion protein (PrP) in which a segment of mouse (Mo) PrP was replaced with the corresponding human (Hu) PrP sequence. The chimeric PrP designated MHu2MPrP, differs from MoPrP by 9 codons between codons 96 and 167. All of the Tg(MHu2MPrP) mice injected with human prions developed neurologic disease. More specifically, the transgenic mice of the invention developed the disease ~200 days after inoculation with brain homogenates from three CJD patients. When inoculated with CJD prions, MHu2MPrP$^{Sc}$ was formed; in contrast MoPrP$^{Sc}$ was produced if Mo prions were inoculated. Tg(MHu2MPrP) mice disclosed herein are useful in the diagnosis, prevention and treatment of human prion diseases. Transgenic mice containing the artificial PrP gene or elevated levels of expression of a native PrP gene from a genetically diverse animal can be used to test samples for prions which might infect such animals. The transgenic and hybrid animals disclosed herein consistently develop the adverse effects of such prions in a relatively short time and are substantially cheaper and easier to maintain than are currently used primate models. Transgenic mice containing a human prion protein gene are designated Tg(HuPrP) and may be crossed with mice with an ablated endogenous prion protein gene which are designated Prnp$^{0/0}$ to obtain a hybrid designated Tg(HuPrP)/Prnp$^{0/0}$.

An object of the invention is to provide a gene which may be artificial or chimeric which gene when inserted into the genome of one animal (e.g., a mouse, hamster or rat) will render the mammal susceptible to infections from prions which naturally only infect a genetically diverse mammal, e.g., human, bovine or ovine.

Another object of the invention is to provide an assay for the detection of prions in a sample.

Another object of the invention is to provide a transgenic animal wherein a host animal includes a genome which has been genetically and artificially transformed to include either the artificial PrP gene of the present invention or elevated levels of expression of a native PrP gene obtained by an enhanced promoter or a high copy number of a native PrP gene of a genetically diverse test animal, such as a human, cow, sheep, pig, dog, cat or chicken.

Another object is to provide a hybrid animal which is obtained by crossing an animal having an ablated endogenous prion protein gene with a transgenic animal containing (1) a chimeric gene or (2) the prion protein gene of a genetically diverse animal which gene may be present at elevated levels.

Another object is to provide a standardized prion preparation produced from harvested brain tissue taken from animals of the invention (that have substantially identical genomes and specifically have substantially identical genetic material related to prions) which animals exhibit symptoms of prion infection after being inoculated with prions which generally only infect a genetically diverse species.

A feature of the invention is that the standardized prion preparations of the invention can be used to consistently inoculate control animals with a known amount and type of prion.

A feature of the invention is that the PrP gene of the host animal can be altered by replacing codons with codons of a test animal at the same relative position which differ from the codons of the host animal, up to and including replacing all the differing codons wherein the codons are replaced in a manner so as to maintain the operability of the gene.

Another object is to provide an artificial PrP gene wherein one or more codons (preferably 1–39 codons) of the PrP gene of a host animal (e.g. a mouse) is replaced with codons of the PrP gene of a genetically diverse test animal (e.g. a human, cow or sheep) in a manner so as to render the host animal susceptible to infection with prions which normally infect only the genetically diverse test animal.

Another object is to provide a chimeric gene comprised of codons encoding the C- and N-terminus of one species of mammal and middle codons of another species of mammal.

Another object of the invention is to provide a transgenic host mammal (which is small, e.g., less than 1 kg when full grown, and inexpensive to maintain) such as a mouse, rat or hamster which includes a chimeric PrP gene which gene includes a portion of the PrP gene from another animal, (which is large, greater than 2 kg when full grown, and expensive to maintain) such as a human, cow, pig, sheep, cat or dog.

Another object of the invention is to provide a transgenic host animal which includes elevated levels of expression of a native PrP gene of a genetically diverse animal wherein the elevated levels of expression are obtained by the inclusion of a high copy number of the PrP gene of the genetically diverse mammal and/or fusing an enhanced promoter to the PrP gene of the genetically diverse animal which transgenic animal may be used by itself to assay for prions or for cross-breeding with an animal which has an ablated endogenous prion protein gene.

An advantage of the present invention is that the transgenic and hybrid animal can be used to assay for the presence of prions in a sample in a manner which is substantially faster, more efficient and cheaper than presently available assay methods.

Another advantage is that transgenic and hybrid animals inoculated with prions of humans can be used as test animals for testing drugs for efficacy in the treatment of humans suffering from diseases resulting from infection with prions.

Another advantage is that the transgenic and hybrid animals can detect prions in a sample at very low levels, e.g., 1 part per million, and even as low as 1 part per billion.

Still another advantage is that the transgenic and hybrid animals provide an assay which is highly accurate, i.e., does not provide false positives and consistently determines the presence of prions.

Yet another advantage is that by increasing the copy number of an exogenous prion protein gene of the invention in a transgenic or hybrid and/or disrupting the endogenous gene of, the incubation time for prion caused disease is decreased.

Another advantage is that the standardized prion preparations of the invention can eliminate the need for extracting brain tissue from mammals which may have been infected with different types of prions and may each have a different genetic make up regarding genetic material related to prions.

Another advantage is that assays of then invention can be carried out more reliably using the standardized prion preparations of the invention.

A feature of the present invention is that the transgenic and hybrid animals injected with a sample containing pathogenic prions will consistently develop the disease effects of the prions within a relatively short time, e.g. about 200 days ±50 days after injection or less.

Another feature is that an artificial gene of the invention preferably contains codons of the PrP gene of a host animal (such as a mouse) with some (but not all) of the codons which differ from the mouse and a second genetically diverse test mammal (such as a human) replacing codons of the first mammal at the same relative positions.

These and other objects, advantages, and features of the invention will become apparent to those persons skilled in the art upon reading the details of the chimeric gene, assay method, and transgenic mouse as more fully described below.

DETAILED DESCRIPTION OF PREFERRED EMBODIMENTS

Figure 1:
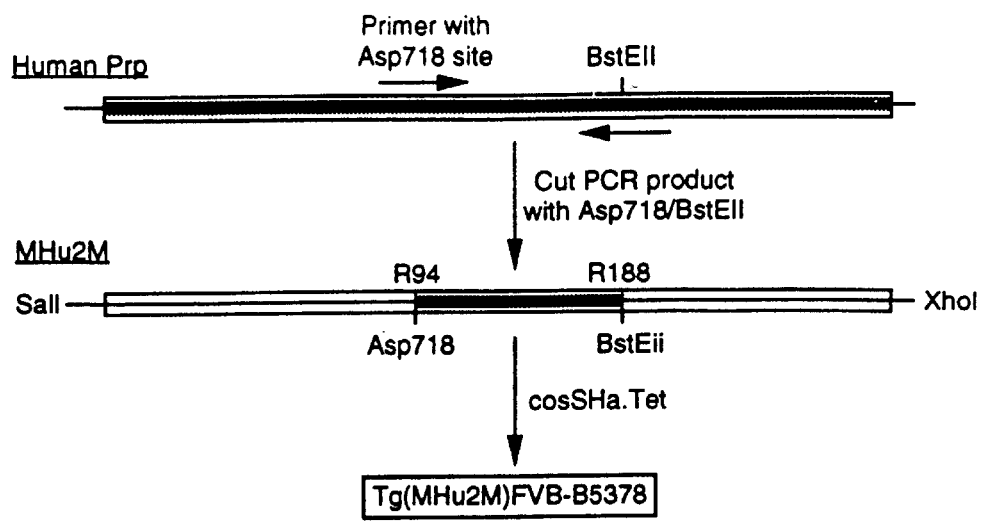
FIG. 1 is a schematic drawing showing the construction of a chimeric MHu2M gene and a transgenic mouse containing same.

Before the present artificial gene, assay methodology, standardized prion preparations, and transgenic and hybrid animals used in the assay are described, it is to be understood that this invention is not limited to particular assay methods, chimeric and artificial genes, prion preparation or transgenic and hybrid animals described, as such methods, genes, preparations, and animals may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The term "prion" shall mean an infectious particle known to cause diseases (spongiform encephalopathies) in humans and animals. The term "prion" is a contraction of the words "protein" and "infection" and the particles are comprised largely if not exclusively of PrPSc molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The terms "PrP gene" and "prion protein gene" are used interchangeably herein to describe genetic material which expresses proteins as shown in FIGS. 3–5 of U.S. Pat. No. 5,565,186 and polymorphisms and mutations such as those listed herein under the subheading "Pathogenic Mutations and Polymorphisms." The PrP gene can be from any animal including the "host" and "test" animals described herein and any and all polymorphisms and mutations thereof, it being recognized that the terms include other such PrP genes that are yet to be discovered.

The terms "standardized prion preparation", "prion preparation", "preparation" and the like are used interchangeably herein to describe a composition containing prions which composition is obtained from brain tissue of mammals which contain substantially the same genetic material as relates to prions, e.g., brain tissue from a set of mammals which exhibit signs of prion disease which mammals (1) include a transgene of the invention; (2) have an ablated endogenous prion protein gene; (3) have a high copy number of prion protein gene from a genetically diverse species; or (4) are hybrids with an ablated endogenous prion protein gene and a prion protein gene from a genetically diverse species. The mammals from which standardized prion preparations are obtained exhibit clinical signs of CNS dysfunction as a result of inoculation with prions and/or due to developing the disease due to their genetically modified make up, e.g., high copy number of prion protein genes.

The term "PrP gene" refers generally to any gene of any species which encodes any form of a prion protein. Some commonly known PrP sequences are described in Gabriel et al., Proc. Natl. Acad. Sci. USA 89:9097–9101 (1992) which is incorporated herein by reference to disclose and describe such sequences.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 3, 4 and 5 of U.S. Pat. No. 5,565,186 with one or more different replacement codons selected from the codons shown in these Figures for humans, cows and sheep replacing mouse codons at the same position, with the proviso that not all the mouse codons are replaced with differing human, cow or sheep codons. Artificial PrP genes of the invention can include not only codons of genetically diverse animals but may include codons and codon sequences not associated with any native PrP gene but which, when inserted into an animal render the animal susceptible to infection with prions which would normally only infect a genetically diverse animal.

The terms "chimeric gene," "chimeric PrP gene", "chimeric prion protein gene" and the like are used interchangeably herein to mean an artificially constructed gene containing the codons of a host animal such as a mouse with one or more of the codons being replaced with corresponding codons from a genetically diverse test animal such as a human, cow or sheep. In one specific example the chimeric gene is comprised of the starting and terminating sequence (i.e., N- and C-terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues.

The term "genetic material related to prions" is intended to cover any genetic material which effects the ability of an animal to become infected with prions. Thus, the term encompasses any "PrP gene", "artificial PrP gene", "chimeric PrP gene" or "ablated PrP gene" which terms are defined herein as well as modification of such which effect the ability of an animal to become infected with prions.

Standardized prion preparations of the invention are produced using animals which all have substantially the same genetic material related to prion so that all of the animals will become infected with the same type of prions and will exhibit signs of infection at about the same time.

The terms "host animal" and "host mammal" are used to describe animals which will have their genome genetically and artificially manipulated so as to include genetic material which is not naturally present within the animal. For example, host animals include mice, hamsters and rats which have their PrP gene altered by the insertion of an artificial gene of the present invention or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal. This is done by including PrP gene sequences of the test animal into the host animal and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "ablated prion protein gene", "disrupted PrP gene", and the like are used interchangeably herein to mean an endogenous prion protein gene which has been altered (e.g., add and/or remove nucleotides) in a manner so as to render the gene inoperative. Examples of non-functional prion protein genes and methods of making such are disclosed in Bueler, H., et al "Normal development of mice lacking the neuronal cell-surface PrP protein" Nature 356, 577–582 (1992) which is incorporated herein by reference. Both alleles of the genes are disrupted.

The terms "hybrid animal", "transgenic hybrid animal" and the like are used interchangeably herein to mean an animal obtained from the cross-breeding of a first animal having an ablated endogenous prion protein gene with a second animal which includes either (1) a chimeric gene or artificial prion protein gene or (2) a prion protein gene from a genetically diverse animal. For example a hybrid mouse is obtained by cross-breeding a mouse with an ablated mouse prion protein gene with a mouse containing (1) human prion protein genes (which may be present in high copy numbers) or (2) chimeric genes. The term hybrid includes any offspring of a hybrid including inbred offspring of two hybrids provided the resulting offspring is susceptible to infection with prions with normal infect only a genetically diverse species.

The terms "susceptible to infection" and "susceptible to infection by prions" and the like are used interchangeably herein to describe a transgenic or hybrid test animal of the invention which has an 80% or greater, preferably 98% or greater, and most preferably a 100% chance of developing a disease if inoculated with prions which would normally only infect a genetically diverse test animal. The terms are used to describe a transgenic or hybrid animal of the invention such as a transgenic mouse Tg(MHu2M) which, without the chimeric PrP gene, would not be susceptible to infection with a human prion (less than 20% chance of infection) but with the chimeric gene is susceptible to infection with human prions (80% to 100% chance of infection).

The term "incubation time" shall mean the time from inoculation of an animal with a prion until the time when the animal first develops detectable symptoms of disease resulting from the infection. A reduced incubation time is one year or less, preferable about 200 days ±50 days or less, more preferably about 50 days ±20 days or less.

Abbreviations used herein include:

CNS for central nervous system;

BSE for bovine spongiform encephalopathy;

CJD for Creutzfeldt-Jakob Disease;

FFI for fatal familial insomnia;

GSS for Gerstmann-Strassler-Scheinker Disease;

Hu for human;

HuPrP for a human prion protein;

Mo for mouse;

MoPrP for a mouse prion protein;

SHa for a Syrian hamster;

SHaPrP for a Syrian hamster prion protein;

Tg for transgenic;

Tg(SHaPrP) for a transgenic mouse containing the PrP gene of a Syrian hamster;

Tg(HuPrP) for transgenic mice containing the complete human PrP gene;

Tg(ShePrP) for transgenic mice containing the complete sheep PrP gene;

Tg(BovPrP) for transgenic mice containing the complete cow PrP gene;

$PrP^{Sc}$ for the scrapie isoform of the prion protein;

$MoPrP^{Sc}$ for the scrapie isoform of the mouse prion protein;

MHu2M for a chimeric mouse/human PrP gene wherein a region of the mouse PrP gene is replaced by a corresponding human sequence which differs from mouse PrP at 9 codons;

Tg(MHu2M) mice are transgenic mice of the invention which include the chimeric MHu2M gene;

$MHu2MPrP^{Sc}$ for the scrapie isoform of the chimeric human/mouse PrP gene;

$PrP^{CJD}$ for the CJD isoform of a PrP gene;

Prn-$p^{0/0}$ for ablation of both alleles of an endogenous prion protein gene, e.g., the MoPrP gene;

Tg($SHaPrP^{+/0}$)81/Prn-$p^{0/0}$ for a particular line (81) of transgenic mice expressing SHaPrP, +/0 indicates heterozygous;

Tg(HuPrP)/$Prnpo^{0/0}$ for a hybrid mouse obtained by crossing a mouse with a human prion protein gene (HuPrP) with a mouse with both alleles of the endogenous prion protein gene disrupted;

Tg(MHu2M)/$Prnp^{0/0}$ for a hybrid mouse obtained by crossing a mouse with a chimeric prion protein gene (MHu2M) with a mouse with both alleles of the endogenous prion protein gene disrupted.

FVB for a standard inbred strain of mice often used in the production of transgenic mice since eggs of FVB mice are relatively large and tolerate microinjection of exogenous DNA relatively well.

GENERAL ASPECTS OF THE INVENTION

The present invention includes several aspects including: (1) an artificial gene comprised of codon sequences which when inserted into the genome of a host animal (e.g. a mouse or hamster) will render the animal susceptible to infection with prions which normally infect only a genetically diverse test animal (e.g. a human, cow or sheep), thereby including genes wherein one or more codons of a naturally occurring PrP gene of a host animal are replaced with corresponding codons of a genetically diverse test animal; (2) a chimeric gene which gene is comprised of the PrP sequence of a gene of a host mammal of a first species (preferably a mouse or hamster) which gene has been modified to include a corresponding segment of a PrP gene of a test animal, preferably a mammal such as a human, cow or sheep; (3) a transgenic mammal containing an artificial gene of the invention such as a transgenic mouse including a chimeric PrP gene wherein a portion of the mouse gene is replaced with a corresponding portion of a human PrP gene thereby rendering the mouse susceptible to infection with human prions; (4) a transgenic mammal with elevated levels of expression of a PrP gene of a genetically diverse mammal wherein the elevated levels of expression are obtained by incorporating a high copy number (30 or more) of a native PrP gene of a genetically diverse test animal and/or the inclusion of an enhanced promoter operatively fused to the PrP gene of a genetically diverse animal; (5) a transgenic hybrid animal which is obtained by crossing a animal having an ablated endogenous prion protein gene with an animal with a chimeric gene as per (2) above or an animal with a prion protein gene of another genetically diverse animal therein e.g., as per (4) above; (6) standardized prion preparations which contain the same amount and type off prions in each preparation; (7) a method of determining whether a sample is infected with prions which method involves inoculating a transgenic or hybrid mammal of the invention with a sample to be tested (and preferably simultaneously inoculating identical test animals with a standardized prion preparation for use as controls) and observing the mammal(s) for a period of time sufficient to determine if the mammal(s) develop(s) symptoms of a disease normally associated with prions; (8) a method of testing the efficacy of a drug in the treatment of disease developed as a result of infection with prions comprising administering a drug to be tested to a transgenic or hybrid animal infected with prions (preferably a standardized prion preparation) and observing and/or testing the mammal to determine if the drug aids in treating or slowing the progress of the disease or its symptoms; and (9) a method for determining the cause of death of an animal comprising inoculating a transgenic or hybrid animal of the invention with body fluid or tissue such as extracted brain tissue from the animal which has died (and preferably inoculating control animals with a standardized preparation of prions) and observing the transgenic or hybrid animal (and control animals) in order to determine if the animal(s) develop(s) symptoms of prion infections.

Preferred host animals are mice and hamsters, with mice being most preferred in that there exists considerable knowledge on the production of transgenic animals. Other possible host animals include those belonging to a genus selected from Mus (e.g. mice), Rattus (e.g. rats), Oryctolagus (e.g. rabbits), and Mesocricetus (e.g. hamsters) and Cavia (e.g., guinea pigs). In general mammals with a normal full grown adult body weight of less than 1 kg which are easy to breed and maintain can be used. The host PrP gene can be changed to include codons from genetically diverse PrP genes from test animals belonging to a genus selected from Bos, Ovis, Sus and Homo. Preferably, a mouse host PrP gene is changed to include codons from a human, cow or sheep PrP gene, with human being most preferred. Humans are preferred because an important object of the invention is to use the animal to test a sample of material to determine if that material has prions which will infect a human and cause a human to develop a CNS disease such as CJD.

The genetic material which makes up the PrP gene is known for a number of different species of animals (see Gabriel et al., *Proc. Natl. Acad. Sci. USA* 89:9097–9101 (1992)). Further, there is considerable homology between the PrP genes in different mammals. For example, see the amino acid sequence of mouse PrP compared to human, cow and sheep PrP in FIGS. 3, 4 and 5 of U.S. Pat. No. 5,565,186 wherein only the differences are shown. Further, note that the segment of PrP gene used to create the MHu2M gene of the present invention will result in encoding of protein which shows a difference between the human and a mouse protein of only nine residues. Although there is considerable genetic homology with respect to PrP genes, the differences are significant in some instances. More specifically, due to small differences in the protein encoded by the PrP gene of different mammals, a prion which will infect one mammal (e.g. a human) will not normally infect a different mammal (e.g. a mouse). Due to this "species barrier", it is not generally possible to use normal animals, (i.e., animal which have not had their genetic material related to prions manipulated) such as mice to determine whether a particular sample contains prions which would normally infect a different species of animal such as a human. The present invention solves this problem in a surprising manner.

Relationships—PrP Genes:Copy Numbers:Genetic Diversity

Commercially useful transgenic animals are preferably small and easy to reproduce; thus, host animals such as mice, hamsters, guinea pigs and rats are preferred, with mice being most preferred. In order for the transgenic animals to be useful, it is necessary for the animals to be susceptible to infection with prions which normally infect only genetically diverse test animals, and in particular animals of commercial significance for testing, such as humans, cows, horses, sheep, pigs, cats, dogs and chickens, with humans being most preferred. Further, for the transgenic and hybrid animals to be useful in a practical and commercial sense, it is necessary for the animals to demonstrate symptoms of the disease within a relatively short period after inoculation, and for a very high percentage of the animals to demonstrate symptoms of the disease after inoculation e.g., 80% or more of inoculated animals develop clinical symptoms of CNS disease with 350 days or less after inoculation.

In producing a transgenic animal having the abovee-scribed characteristics, we noted a number of relationships of significance. First, when the entire PrP gene of a test animal (such as a human) is made functional in the host animal (such as a mouse) the resulting transgenic animal (with a low copy number of human PrP genes) is not susceptible to infection with human prions. Second, we found that infection would occur if the endogenous PrP gene of the host animal is ablated. Third, when only some of the codons differing between the host and the test animal are switched, the resulting transgenic animal is susceptible to infection with prions which normally only infect the test animal.

Fourth, we noticed that, as the copy number of the artificial gene in the transgenic animal is increased, the incubation time decreases. With this knowledge, we deduced that it is possible to produce a transgenic animal wherein all of the PrP gene of the host animal is replaced with the PrP gene of a test animal to obtain a useful transgenic animal which is susceptible to infection with prions which normally only infect the test animal by substantially increasing the copy number of the test animal's PrP gene in the host animal. For example, a transgenic mouse which includes the entire PrP gene of a human in a relatively low copy number (e.g. 1 to 4) is not susceptible to infection with human prions (unless the endogenous mouse PrP gene is ablated). However, if the transgenic mouse includes a very high copy number of a human gene (e.g. 30–300 copies), the resulting transgenic animal is susceptible to infection with human prions. Further, when a host animal such as a mouse has only a portion of its PrP gene replaced with a corresponding portion of a test animal such as a human, the resulting transgenic animal is highly susceptible to infection with prions which normally infect only the test animal. This is true even if the chimeric gene is present in the transgenic animal in a relatively low copy number (e.g. 1 to 4 copies) resulting in low expression of MHu2M $PrP_C$.

Lastly, in order to reduce incubation time hybrid mice were created by crossing mice with ablated prion protein genes with transgenic mice which (1) included a prion protein gene from a genetically diverse animal e.g., a human or (2) include a chimeric or artificial gene of the present invention. The chimeric gene and/or PrP gene from genetically diverse test animal may be present in high copy number. The copy number can be increased in order to reduce incubation time provided the copy number is not increased so far that the animal becomes spontaneously ill, i.e., become ill without inoculation with prions.

Based on the above, it can be understood that the preferred transgenic animals of the invention are (1) animals such as mice which include a chimeric PrP gene, i.e., only a portion, but not all, of their PrP gene replaced with a corresponding portion of the PrP gene of a test animal or (2) animals with an ablated endogenous PrP gene and a PrP gene from another animal.

It is preferable to include chimeric genes within the transgenic animal in a relatively high copy number, in that increasing the copy number tends to decrease the incubation time for the disease once the animal is inoculated with material containing prions. Notwithstanding such, we now understand that, when the copy number is increased to very high numbers (e.g. 100 copies and above), the transgenic animals may spontaneously demonstrate symptoms of prion disease. Thus, a most preferred transgenic animal of the invention will include a chimeric PrP gene in a sufficiently high copy number so as to shorten the incubation time (e.g. 50 copies ±25) but in a sufficiently low number so as to not initiate spontaneous symptoms characteristic of prion diseases (e.g., not more than 100 copies). It will be understood by those skilled in the art that the number of copies necessary in order to obtain elevated levels of expression of the PrP gene will vary depending upon the particular gene inserted into the particular host. Adjustments can be made to reduce the copy number if the resulting transgenic animals become spontaneously ill. Alternatively adjustments can be made to increase the copy number if the resulting transgenic animals are not subject to infection with prions which normally infect only a genetically diverse animal. Further, adjustments can be made with respect to the use of specific types of enhanced promoters in order to elevate the levels of expression without increasing copy numbers. Specific types of enhanced promoters are known such as neuronal enolase promoters which would provide enhanced expression to the PrP gene without increased copy numbers. The enhanced promoters may operate constitutively or inducibly.

The ability to successfully produce a transgenic animal is related, in part, to the genetic diversity between the host animal and the test animal as regards their respective PrP genes. For example, the PrP gene of a mouse and a hamster are relatively similar in that they differ only at 16 codons out of a total of 254 codons. When the genetic similarity of the PrP genes are this close, it is possible to include the entire PrP gene sequence of the test animal into the host animal and render the host animal susceptible to prions which normally only infect the test animal. However, such is not the case when the host animal and test animal are genetically diverse, i.e. differ in PrP genes by 20 or more codons. Thus, when a mouse PrP gene is completely replaced with a genetically diverse PrP gene, such as that of a human, the resulting transgenic mouse will not be susceptible to infection with human prions unless (1) the endogenous PrP gene of the mouse is ablated or (2) the human gene is present in the mouse in a relatively high copy number—which high copy number may result in spontaneous development of disease.

To solve the problem of being able to decrease the copy number such that the animal would not spontaneously become sick, and yet allow the animal to become sick when inoculated with human prions, we created a chimeric gene which includes only a portion of the human PrP gene in the mouse PrP gene. A more specific description of how the species barrier was broken in accordance with the present invention is provided below.

When transgenic animals are produced by placing the entire human prion protein gene into that of a mouse the resulting transgenic mouse does not become consistently ill in a short period of time when inoculated with prions which generally only infect humans i.e., is not susceptible to infection with human prions. The inability to become infected appears to be related to the presence of the endogenous mouse prion protein gene. When a mouse with a human prion protein gene is crossed with a mouse with a disrupted endogenous mouse gene the hybrid offspring are infected by prions which normally only infect humans. Such hybrid mice will consistently become infected and exhibit an incubation time of less than 300 days, preferably 250 or less ±50 days.

Species Barrier Broken

The transmission of human CJD to apes and monkeys 1.5–3 years after intracerebral inoculation provided considerable interest in the causes of neurodegenerative diseases [Gibbs, Jr. et al., *Science* 161:388–389 (1968)]. Humans are not genetically diverse from apes and monkeys which accounts for the cross-species infectivity, although with a long incubation time. While the high cost of caring for nonhuman primates prevented extensive studies of the human prion diseases, the transmissibility of these diseases stimulated studies of the animal prion analogues in rodents [Manuelidis et al., *Proc. Natl. Acad. Sci. USA* 75:3422–3436 (1978); Manuelidis et al., *Proc. Natl. Acad. Sci. USA* 73:223–227 (1976); Tateishi et al., *Ann. Neurol.* 5:581–584 (1979)].

The present disclosure opens a new frontier in the investigation of the human prion diseases since transmission studies can now be performed relatively rapidly in genetically altered mammals such as Tg(MHu2M) mice that are relatively inexpensive to maintain. For the first time, endpoint titrations of prions in multiple human body tissues and fluids can be performed and standard curves constructed for more economical incubation time assays. The information derived from such studies of human prions will be useful in the management of CJD patients who are thought to pose some risk to relatives, physicians, nurses and clinical laboratory technicians [Berger et al., *Neurology* 43:205–206 (1993); Ridley et al., *Lancet* 341:641–642 (1993)].

In studies of human prion diseases with apes and monkeys, the use of one or two, or rarely three, animals as recipients for a single inoculum has presented a significant problem in evaluating the transmissibility of a particular inoculum from an individual patient. The transgenic mice contain a chimeric prion protein gene, e.g., Tg(MHu2M) mice, and hybrid mice e.g., Tg(HuPrP)/Prnp$^{0/0}$ described here obviate many of the problems created by using non-human primates.

These results demonstrate the "universality" of the MHu2M transgene for transmission studies with other types of transgenic animals and other prion inocula. For example, it may be most efficient to use mice expressing MHu2MPrP transgenes coding for either a methionine or valine at codon 129, and by doing so, match the genotype of the Tg mouse (with respect to codon 129) with the genotype of the individual from which the inoculum is derived. Homozygosity at the codon 129 polymorphism has a profound influence on the incidence of sporadic CJD [Palmer et al., *Nature* 352:340–342 (1991)]. The MHu2MPrP transgene encodes a Met at codon 129 and the iatrogenic CJD case was homozygous for Met [Collinge et al., *Lancet* 337:1441–1442 (1991)].

To break the species barrier we have created an artificial PrP gene which, when inserted into a host mammal (such as a mouse) renders that mammal susceptible to infection with prions which normally infect only a genetically diverse test mammal (e.g. a human, cow or sheep). The artificial PrP gene may include the natural PrP gene sequence of the host animal with one or more (preferably less than 40) codon sequences being replaced with other codon sequences such as corresponding codons of a genetically diverse mammal (e.g. a human, cow or sheep).

In a specific example of the invention the species barrier is broken by inserting into a mammal (a mouse) the chimeric gene (MHu2M) which is shown being assembled schematically in FIG. 1. In order to produce the chimeric gene, it is first necessary to obtain nucleotide sequences which encode human PrP. The human PrP genes are then subjected to the conventional PCR procedures in order to produce large numbers of copies of the gene or portions of the gene. The PCR product is then isolated, specific restriction sites are added and the copied product is subjected to specific endonucleases in order to remove a middle section of the human PrP gene. Specifically, restriction sites are added such that when the PCR product is subjected to endonucleases such as Asp718 as well as BstEII, a section of the gene is cut out. The use of these two endonucleases will remove a center portion of the human PrP gene (codons 94–188) which portion encodes amino acid residues 94 through 188. Endonucleases are also used to remove a corresponding center portion of the mouse PrP gene. The removed center portion of the mouse gene is then discarded and the center portion obtained from the human PrP gene is fused into the mouse gene to produce a chimeric human/mouse gene. Details of how the specific MHu2M gene was produced are described in Example 1 and shown in FIG. 1.

Figure 2:
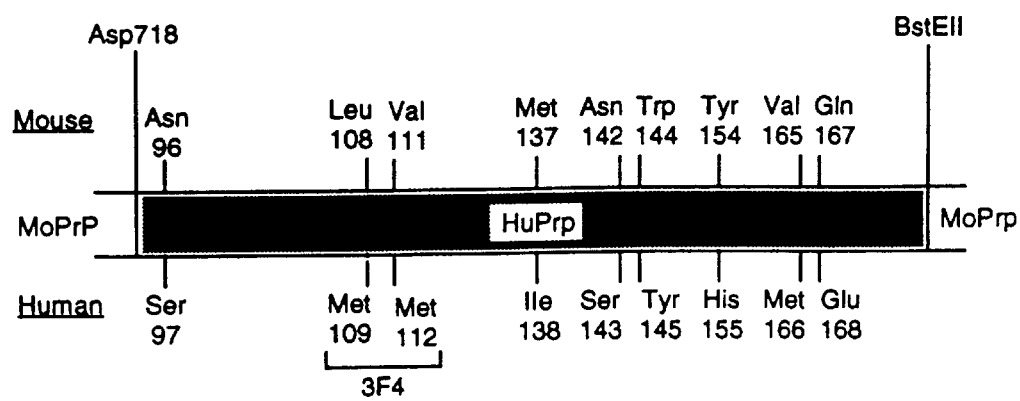
FIG. 2 is a schematic view of a portion of PrP proteins showing the differences between a normal, wild-type human PrP protein and a normal, wild-type mouse PrP protein.

As shown with FIG. 2, there is a high degree of homology between the removed center portion of the human PrP gene and the segment of the mouse PrP gene which is replaced. Specifically, the segments differ at nine codons. Thus, when the genetic material is expressed, the resulting chimeric MHu2M protein will differ from MoPrP at 9 residues. These residues and their positions are shown in FIG. 2. After the chimeric gene is produced, it can be microinjected into a mouse egg using known technology as described within Scott et al., *Cell* 59:847–857 (1989) and Scott et al., *Protein Sci.* 1:986–997 (1992) and see also WO91/19810 published Dec. 22, 1991 as well as other publications relating to the production of transgenic mice cited therein and known to those skilled in the art. The injected mouse egg is then implanted into a mouse using known procedures. Multiple eggs can be implanted into a single mouse and known procedures can be used to determine whether the resulting offspring are transgenic mice which include the chimeric gene within their genome. Details of this procedure are described in Example 1.

We have successfully broken the "species barrier" by producing a chimeric PrP gene wherein a middle portion of the mouse PrP gene is replaced with a corresponding middle portion of a human PrP gene thereby leaving the C- and N-terminus of the mouse PrP gene intact. However, other segments of the mouse PrP gene can be replaced with other homologous segments of the human PrP gene and obtain a transgenic mouse which is subject to being readily infected with human prions. Thus, the invention is not limited to the particular chimeric gene MHu2M or chimeric mice produced using this gene. The invention includes all types of transgenic animals which include artificial genes wherein the artificial gene renders the transgenic animal susceptible to infection with prions which normally infect only a genetically diverse animal.

Numerous specific examples of artificial genes of the invention can be deduced from reviewing FIGS. 3, 4 and 5 of U.S. Pat. No. 5,565,186. Specifically, one may start with the basic PrP gene of a mouse (as the host animal) which animal is to become the transgenic animal. Thereafter, one or more codons of the mouse gene may be replaced with one or more corresponding codons of a human, bovine or sheep PrP gene which codon is different from the corresponding codon of the mouse gene but at the same relative position in the gene. By showing that it is possible to break the "species barrier" by creating a particular chimeric gene whereby transgenic mice can test for the presence of human prions we have opened the door for the creation of other transgenic animals which will include other artificial PrP genes which, for example, can allow for the testing for the presence of bovine or ovine prions in a sample.

High Copy Numbers

The present invention includes transgenic animals wherein the host animal has its genome changed to include multiple copies of the entire PrP gene of a genetically diverse test animal. Thus, for example, the invention includes transgenic mice and hamsters altered to include two fold or higher levels of expression of the PrP gene of a genetically diverse test animal such as a human, cow or sheep. The two fold or higher levels of expression can be obtained by including higher copy numbers such as 30 or more copies of the PrP gene of the genetically diverse test animal and/or by including an enhanced promoter which elevates the level of expression of even a low copy number of the gene.

Hybrid Animals

Hybrid animals of the invention can be produced by crossing an animal with an ablated endogenous prion protein gene with either of the transgenic animals mentioned above. For example, a mouse containing a human/mouse chimeric prion is crossed with a mouse with a disrupted endogenous prion protein gene e.g., Tg(Prnp$^{0/0}$). Alternatively, a mouse containing a high copy number of human prion protein genes (e.g., 50±25) is crossed with a mouse with a disrupted endogenous prion protein gene e.g., Tg(Prnp$^{0/0}$) to obtain a hybrid Tg(HuPrP)/Prnp$^{0/0}$. A variety of different hybrids can be obtained by crossing an animal with an ablated prion protein gene (i.e., a null prion background) with different transgenic animals with different prion protein genes. When successful hybrids are obtained they can be crossed to produce other animals which for the purpose of the disclosure are also considered hybrids if they are susceptible to infection with prions which generally only infect a genetically diverse species. A null prion background means that more than 50% of the endogenous prion protein genes are disrupted, preferable more than 80%, more preferable more than 90% and most preferable 100%.

Tg(MHu2M) Mice with Shorter Incubation Times

The incubation time of Tg(MHu2M) mice inoculated with Hu prions is now about 200 days or less ±50 days, which can be reduced substantially by increasing the copy number of the MHu2M gene (e.g. to about 50±25) and thereby obtaining an elevated level of expression. In Tg(SHaPrP) mice, the level of SHaPrP transgene expression was found to be inversely proportional to the length of the scrapie incubation time after inoculation with SHa prions [Prusiner et al., Cell 63:673–686 (1990)]. Thus, producing Tg(MHu2M) mice with higher levels of transgene expression is a means of substantially reducing incubation time.

Based on other studies with Tg mice harboring a hamster PrP gene we have shown that the incubation period for Tg mice (or any host) with a chimeric or artificial PrP gene can approach 30 days or less. For example, Tg(SHaPrP)/Prnp$^{0/0}$ mice containing more than 100 copies of a exogenous PrP gene material have an incubation time of approximately 25 days.

In addition, removing MoPrP$^C$ by crossing Tg(MHu2M) mice onto an ablated background (Prn-p$^{0/0}$) may also reduce the incubation time since Tg(SHaPrP$^{+/0}$)81/Prn-p$^{0/0}$ mice exhibit a 30% reduction in incubation times compared to Tg(SHaPrP$^{+/0}$)81/Prn-p$^{+/+}$ mice [Büeler et al., Cell 73:1339–1347 (1993). Prusiner et. al., Proc. Natl. Acad. Sci. USA 90:10608–10612 November 1993. Accordingly, we have also used fertilized eggs from mice in which the endogenous PrP gene has been ablated as recipients for microinjection of the MHu2M PrP construct.

By systematically altering the extent and position of the substitutions in other chimeric Hu/Mo PrP constructs, it is possible to further enhance the susceptibility of Tg mice to Hu prions as reflected by shortened incubation times. Shortening the incubation time is a worthwhile goal for the facilitation of many future studies in prion research and for the evaluation of pharmaceuticals, foods, tissues, organs, grafts, cosmetics and other substances—particularly substances which have some portion derived from an animal, such as a human, which animal might be infected with prions.

In general, there is an inverse relationship between the number of copies of a chimeric or artificial PrP gene and the incubation time of disease after inoculation of the transgenic animal with prions. Specific MHu2M mice disclosed herein have only 3 or 4 copies of the MHu2M gene. The number of copies can be increased to 30 to 400, thereby significantly reducing the incubation time from about 200 days to 50 days ±20 days or less. Those skilled in the art will understand that the copy number should not be increased to a point where the animal will spontaneously develop disease.

Pathogenic Mutations and Polymorphisms

There are a number of known pathogenic mutations in the human PrP gene. Further, there are known polymorphisms in the human, sheep and bovine PrP genes. The following is a list of such mutations and polymorphisms:

| Pathogenic human mutations | Human Polymorphisms | Sheep Polymorphisms | Bovine Polymorphisms |
| --- | --- | --- | --- |
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

The DNA sequence of the human, sheep and cow PrP genes have been determined allowing, in each case, the prediction of the complete amino acid sequence of their respective prion proteins. The normal amino acid sequence which occurs in the vast majority of individuals is referred to as the wild-type PrP sequence. This wild-type sequence is subject to certain characteristic polymorphic variations. In the case of human PrP, two polymorphic amino acids occur at residues 129 (Met/Val) and 219 (Glu/Lys). Sheep PrP has two amino acid polymorphisms at residues 171 and 136, while bovine PrP has either five or six repeats of an eight amino acid motif sequence in the amino terminal region of the mature prion protein. While none of these polymorphisms are of themselves pathogenic, they appear to influence prion diseases. Distinct from these normal variations of the wild-type prion proteins, certain mutations of the human PrP gene which alter either specific amino acid residues of PrP or the number of octarepeats have been identified which segregate with inherited human prion diseases.

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., Proc. Natl. Acad. Sci. USA 89:9097–9101 (1992). The sequence for the Syrian hamster is published in Basler et al., Cell 46:417–428 (1986). The PrP gene of sheep is published by Goldmann et al., Proc. Natl. Acad. Sci. USA 87:2476–2480 (1990). The PrP gene sequence for bovine is published in Goldmann et al., J. Gen. Virol. 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). These publications are all incorporated herein by reference to disclose and describe the PrP gene and PrP amino acid sequences.

Differences in the Conversion of MHu2MPrP$^C$ and HuPrP$^C$ into the Scrapie Isoform in Mice The fundamental event in prion propagation seems to be the conversion of PrP$^C$, which contains ~43% α-helix and is devoid of β-sheet, into PrP$^{Sc}$ which has ~44% β-sheet [Pan et al., *Proc. Natl. Acad. Sci. USA* 90:10962–10966 (1993)]. From the results of Tg(SHaPrP) mouse studies, this process is thought to involve the formation of a complex between PrP$^{Sc}$ and the homotypic substrate PrP$^C$ [Prusiner et al., *Cell* 63:673–686 (1990)]. Attempts to mix PrP$^{Sc}$ with PrP$^C$ have failed to produce nascent PrP$^{Sc}$ [Raeber et al., *J. Virol.* 66:6155–6163 (1992)], raising the possibility that proteins such as chaperons might be involved in catalyzing the conformational changes that feature in the formation of PrP$^{Sc}$. One explanation for the difference in susceptibility of Tg(MHu2M) and Tg(HuPrP) mice to Hu prions in mice may be that mouse chaperons catalyzing the refolding of PrP$^C$ into PrP$^{Sc}$ can recognize MHu2MPrP much more readily than HuPrP.

Another possibility is that sequences at the N- or C-terminus of HuPrP inhibit the formation of PrP$^{Sc}$ in murine cells. To test this possibility, HuPrP sequences are substituted for the Mo sequences at each terminus of MHu2MPrP. Comparison of the PrP sequences in many mammals around the GPI anchor addition site (codons 227–235) reveals an interesting difference of four amino acids between rodents and primates [Stahl et al., *Biochemistry* 31:5043–5053 (1992)]. In support of this hypothesis is that rodents also differ from ruminants including sheep and cattle at this site; sheep prions have failed to transmit neurodegeneration to Tg(ShePrP). In these experiments the transgenic mice expressed the entire sheep PrP gene.

In contrast to Tg(MHu2M) mice, the overall transmission rate of Hu prion inocula from a wide variety of sources was less than 10% in Tg(HuPrP) mice, no different from the rate observed in non-Tg mice. Likewise the conversion of HuPrP$^C$ into HuPrP$^{Sc}$ in Tg(HuPrP) mice appears to be a relatively infrequent event similar to the rare conversion of MoPrP$^C$ to PrP$^{Sc}$ in response to human prions. The low rates of transmission in these mice do not seem to be a consequence of low titers of human prion titers: two inocula which failed to cause disease in Tg(HuPrP) mice transmitted to 100% of inoculated Tg(MHu2M) animals.

Another possible explanation for not getting infection with Tg(HuPrP) mice is that the conversion of PrP$^c$ into PrP$^{Sc}$ requires the participation of another macromolecule. We assume that this macromolecule is a protein and have provisionally designated it as "protein X". Like the binding of PrP$^C$ to PrP$^{Sc}$ which is most efficient when the two isoforms have the same sequence (Prusiner et al., 1990), the binding of PrP$^C$ to protein X seems to exhibit the highest affinity when these two proteins are from the same species.

While our results demonstrate that PrP$^{Sc}$ binds to PrP$^C$ in a region delimited by codons 96 and 167, they also suggest that PrP$^C$ may bind protein X through a second domain composed of residues lying between 215 and 230 at the C-terminus. Such a model can explain why chimeric MHu2MPrP$^C$ but not HuPrP$^C$ is converted into PrP$^{Sc}$ in the presence of MoPrP$^C$ and why HuPrP$^C$ is converted into PrP$^{Sc}$ in the absence of MoPrP$^C$. This model of prion propagation involving protein X can also explain why inherited forms of prion disease modeled in mice with the GSS mutation at codon 102 can be produced with Tg mice expressing the P102L point mutation in MoPrP (Hsiao et al., 1994; Hsiao et al., 1990) and chimeric MHu2MPrP but not HuPrP as described here. The proposed model is consistent with additional observations showing that Tg(MHu2M) mice were resistant to Hu prions from a patient with GSS who carried the P102L mutation but were susceptible to prions from patients with familial CJD who harbor the E200K mutation; however, Tg(MHu2M-P101L) mice were susceptible to GSS prions. These findings and other studies reported here demonstrate that single amino acid mismatches at codon 102 or 129 prolong the incubation time; whereas, a mismatch at codon 200 does not.

It seems reasonable to propose that protein X may function as a molecular chaperon in the refolding of PrP$^C$ into PrP$^{Sc}$; the apparent lack of PrP$^{Sc}$ binding to protein X is consistent with it being the product of a chaperon-mediated reaction. Attempts to identify a chemical modification that distinguishes PrP$^{Sc}$ have been unsuccessful (Stahl et al., 1993); yet, the secondary structure of PrP$^{Sc}$ contains a substantial amount of β-sheet which is not present in PrP$^C$ (Pan et al., 1993; Safar et al., 1993). These findings argue that a conformational change underlies the conversion of PrP$^C$ into PrP$^{Sc}$ and thus, it is likely that a molecular chaperon features in the unfolding of PrP$^C$ and its refolding into PrP$^{Sc}$.

"Strains" of Human Prions

Studies in rodents have shown that prion strains produce different patterns of PrP$^{Sc}$ accumulation [Hecker et al., *Genes & Development* 6:1213–1228 (1992); DeArmond et al., *Proc. Natl. Acad. Sci. USA* 90:6449–6453 (1993)]; which can be dramatically changed by the sequence of PrP$^C$ [Carlson et al., *Proc. Natl. Acad. Sci. USA* in press (1994)]. The molecular basis of prion diversity has for many years been attributed to a scrapie specific nucleic acid [Bruce et al., *J. Gen. Virol.* 68:79–89 (1987)] but none has been found [Meyer et al., *J. Gen. Virol.* 72:37–49 (1991); Kellings et al., *J. Gen. Virol.* 73:1025–1029 (1992)]. Other hypotheses to explain prion strains include variations in PrP Asn-linked sugar chains [Hecker et al., *Genes & Development* 6:1213–1228 (1992)] and multiple conformers of PrP$^{Sc}$ [Prusiner, S. B., *Science* 252:1515–1522 (1991)]. The patterns of PrP$^{Sc}$ in Tg(MHu2M) mice were remarkably similar for the three inocula from humans dying of CJD.

The patterns of PrP$^{Sc}$ accumulation in the brains of inoculated Tg(MHu2M) mice were markedly different for RML prions and Hu prions. However, RML prion inocula containing MoPrP$^{Sc}$ stimulated the formation of more MoPrP$^{Sc}$ while Hu prion inocula containing HuPrP$^{CJD}$ triggered production of MHu2MPrP$^{Sc}$. The distribution of neuropathological changes characterized by neuronal vacuolation and astrocytic gliosis is similar to the patterns of PrP$^{Sc}$ accumulation in the brains of Tg(MHu2M) mice inoculated with RML prions or Hu prions.

New Approaches To Investigating Human Prion Diseases

The remarkable sensitivity of Tg(MHu2M) mice to Hu prions represents an important advance in neurodegenerative disease research. Based on the present disclosure regarding chimeric Hu/Mo PrP transgenes we conceived of a similar approach to the construction of Tg ice susceptible to BSE and scrapie sheep prions. Such would be useful in detecting prion diseases in domestic animals. The importance of animal prion diseases is illustrated by BSE or "mad cow disease" in Great Britain, where >150,000 cattle have died. This prion disease BSE is thought to have originated with cattle consuming meat and bone meal produced from sheep offal containing scrapie prions [Wilesmith, J. W., *Semin. Viro.* 2:239–245].

The BSE epidemic has led to considerable concern about the safety for humans of European beef and other cattle products. Epidemiologic studies over the past two decades have provided much data arguing that humans are unlikely to contract CJD from scrapie-infected sheep products [Harries-Jones et al., *J. Neurol. Neurosurg. Psychiatry* 51:1113–1119 (1988); Cousens et al., *J. Neurol. Neurosurg. Psychiatry* 53:459–465 (1990); Brown et al., *Neurology* 37:895–904 (1987)]. There are seven amino acid substitutions which distinguish bovine from sheep PrP which must be considered in drawing conclusions from sheep scrapie about the risk factors to humans from BSE. Whether any of these seven amino acid substitutions render bovine prions permissive in humans remains to be established. It may be that Tg(MHu2M) mice are susceptible to bovine as well as sheep prions. Of perhaps even greater importance, Tg(MHu2M) mice have immediate application in the testing of pharmaceuticals for human prion contamination. The Tg(MHu2M) mice described here provide a sensitive, reliable and economical bioassay for detecting the presence of human prions.

Standardized Prion Preparation

Standardized prion preparations are produced for use in assays so as to improve the reliability of the assay. Although the preparation can be obtained from any animal it is preferably obtained from a host animal which has brain material containing prions of a test animal. For example, a Tg mouse containing a human prion protein gene can produce human prions and the brain of such a mouse can be used to create a standardized human prion preparation. Further, in that the preparation is to be a "standard" it is preferably obtained from a battery (e.g., 100; 1,000, or more animals) of substantial identical animals. For example, 100 mice all containing a very high copy number of human PrP genes (all polymorphisms and mutations) would spontaneously develop disease and the brain tissue from each could be combined to make a useful standardized prion preparation.

Standardized prion preparations can be produced using any of the modified host mammals of the present invention. For example, standardized prion preparations could be produced using mice, rats, hamsters, or guinea pigs which are genetically modified per the present invention so that they are susceptible to infection with prions which prions would generally only infect genetically diverse species such as a human, cow, sheep or horse and which modified host mammals will develop clinical signs of CNS dysfunction within a period of time of 350 days or less after inoculation with prions. The most preferred host mammal is a mouse in part because they are inexpensive to use and because a greater amount of experience has been obtained with respect to production of transgenic mice than with respect to the production of other types of host animals.

Once an appropriate type of host is chosen, such as a mouse, the next step is to choose the appropriate type of genetic manipulation to be utilized to produce a standardized prion formulation. For example, the mice may be mice which are genetically modified by the insertion of a chimeric gene of the invention. Within this group the mice might be modified by including high copy numbers of the chimeric gene and/or by the inclusion of multiple promoters in order to increase the level of expression of the chimeric gene. Alternatively, hybrid mice of the invention could be used wherein mice which have the endogenous PrP gene ablated are crossed with mice which have a human PrP gene inserted into their genome. There are, of course, various subcategories of such hybrid mice. For example, the human PrP gene may be inserted in a high copy number an/or used with multiple promoters to enhance expression. In yet another alternative the mice could be produced by inserting multiple different PrP genes into the genome so as to create mice which are susceptible to infection with a variety of different prions, i.e., which generally infect two or more types of test animals. For example, a mouse could be created which included a chimeric gene including part of the sequence of a human, a separate chimeric gene which included part of the sequence of a cow and still another chimeric gene which included part of the sequence of a sheep. If all three different types of chimeric genes were inserted into the genome of the mouse the mouse would be susceptible to infection with prions which generally only infect a human, cow and sheep.

After choosing the appropriate mammal (e.g., a mouse) and the appropriate mode of genetic modification (e.g., inserting a chimeric PrP gene) the next step is to produce a large number of such mammals which are substantially identical in terms of genetic material related to prions. More specifically, each of the mice produced will include an identical chimeric gene present in the genome in substantially the same copy number. The mice should be sufficiently identical genetically in terms of genetic material related to prions that 95% or more of the mice will develop clinical signs of CNS dysfunction within 350 days or less after inoculation and all of the mice will develop such CNS dysfunction at approximately the same time e.g., within ±30 days of each other.

Once a large group e.g., 50 or more, more preferably 100 or more, still more preferably 500 or more of such mice are produced. The next step is to inoculate the mice with prions which generally only infect a genetically diverse mammal e.g., prions from a human, sheep, cow or horse. The amounts given to different groups of mammals could be varied. After inoculating the mammals with the prions the mammals are observed until the mammals exhibit symptoms of prion infection e.g., clinical signs of CNS dysfunction. After exhibiting the symptoms of prion infection the brain or at least a portion of the brain tissue of each of the mammals is extracted. The extracted brain tissue is homogenized which provides the standardized prion preparation.

As an alternative to inoculating the group of transgenic mice with prions from a genetically diverse animal it is possible to produce mice which spontaneously develop prion related diseases. This can be done, for example, by including extremely high copy numbers of a human PrP gene into a mouse genome. When the copy number is raised to, for example, 100 or more copies, the mouse will spontaneously develop clinical signs of CNS dysfunction and have, within its brain tissue, prions which are capable of infecting humans. The brains of these animals or portions of the brain tissue of these animals can be extracted and homogenized to produce a standardized prion preparation.

The standardized prion preparations of the invention can be used directly or can be diluted and titered in a manner so as to provide for a variety of different positive controls. More specifically, various known amounts of such standardized preparation can be used to inoculate a first set of transgenic control mice. A second set of substantially identical mice are inoculated with a material to be tested i.e., a material which may contain prions. A third group of substantially identical mice are not injected with any material. The three groups are then observed. The third group, should, of course not become ill in that the mice are not injected with any material. If such mice do become ill the assay is not accurate probably due to the result of producing mice which spontaneously develop disease. If the first group, injected with a standardized preparation, do not become ill the assay is also inaccurate probably because the mice have not been correctly created so as to become ill when inoculated with prions which generally only infect a genetically diverse mammal. However, if the first group does become ill and the third group does not become ill the assay can be presumed to be accurate. Thus, if the second group does not become ill the test material does not contain prions and if the second group does become ill the test material does contain prions.

By using standardized prion preparations of the invention it is possible to create extremely dilute compositions containing the prions. For example, a composition containing one part per million or less or even one part per billion or less can be created. Such a composition can be used to test the sensitivity of the transgenic mice of the invention in detecting the presence of prions in the sample.

Prion preparations of the present invention are desirable in that they will include a constant amount of prions and are extracted from an isogeneic background. Accordingly, contaminates in the preparations will be constant and controllable. Standardized prion preparations of the invention will be useful in the carrying out of bioassays in order to determine the presence, if any, of prions in various pharmaceuticals, whole blood, blood fractions, foods, cosmetics, organs and in particular any material which is derived from an animal (living or dead) such as organs, blood and products thereof derived from living or dead humans. Thus, standardized prion preparations of the invention will be valuable in validating purification protocols where preparations are spiked and reductions in teeter measured for a particular process.

Chimeric PrP Gene

Since the fundamental event underlying prion propagation seems to be a conformational change in PrP [Pan et al., *Proc. Natl. Acad. Sci. USA* 90:10962–10966 (1993)] and mouse PrP differs from human PrP at 31 positions out of 254 [Kretzschmar et al., *DNA* 5:315–324 (1986)], we constructed modified PrP transgenes. Chimeric SHa/Mo transgenes have produced prions with new properties, the most useful being the chimeric SHa/Mo transgene labeled MH2M which carries 5 amino acid substitutions found in SHaPrP lying between codons 94 and 188. [Scott et al., *Cell* 73:979–988 (1993)]. We made an analogous chimeric human/mouse PrP gene, which we call MHu2M, in which the same region of the mouse gene is replaced by the corresponding human sequence which differs from mouse PrP at 9 codons as is shown in FIG. 2.

Mice expressing the MHu2M chimeric transgene are susceptible to human prions after abbreviated incubation times. More specifically, the transgenic mice of the present invention which include the chimeric MHu2M gene will, after inoculation with human prions, develop disease symptoms attributed to the prions within about 200 days ±50 days. Further, 80% or more the transgenic mice of the invention inoculated with human prions will develop symptoms of the disease, more preferably 98% or more of the mice will develop symptoms of the disease. According to experiments carried out, 100% of the transgenic MHu2M mice inoculated with human prions actually developed symptoms of the disease in about 200 days or less ±50 days.

These findings indicate that murine cells cannot readily convert HuPrP$^C$ into HuPrP$^{Sc}$ but they can process MHu2MPrP$^C$ into MHu2MPrP$^{Sc}$. Since Tg(MHu2M) mice develop neurodegeneration more rapidly than monkeys, they provide a preferred host for bioassays of infectivity in tissues of humans dying of prion diseases. The Tg(MHu2M) mice disclosed herein provide an excellent system for assessing the sterility of pharmaceuticals as well as tissue and organ grafts prepared from human sources. Other transgenic mice which include the prion protein gene of the animal in danger of infection can be used to test samples for prion diseases which can infect domestic animals such as sheep and cattle.

Samples for assay may be obtained from any source, including animal and plant sources. Such samples are prepared for inoculation into the transgenic mammal by the methods described herein or methods known to those skilled in the art.

Chimeric MHu2M Gene

FIG. 1 is shown regarding how to create the chimeric MHu2M gene. At first, we engineered a new KpnI site in the HuPrP ORF cassette (shown shaded), changing nucleotide 282 from a cytosine to a thymine residue by PCR-mediated mutagenesis. This mutagenic change conserves the a mino acid sequence of HuPrP. A second oligonucleotide primer complimentary to DNA sequences around the BstEll-cut product was used to replace the corresponding MoPrP gene fragment (the MoPrP gene is unshaded) creating the hybrid gene MHu2M. Microinjection of a cosSHa.Tet construct bearing this expression cassette resulted in founder animal Tg(MHu2M)FVB-B5378.

An expanded representation of the region of MHu2MPrP between codons 94 and 188 which is flanked by MoPrP sequences (FIG. 2). MHu2MPrP differs from MoPrP by nine amino acids in the region between amino acids 96 and 167. These amino acid residues which are derived from HuPrP are shown on the lower section of the diagram; the amino acids at the same position of MoPrP are shown above. The discrepancy of amino acid positions is due to MoPrP having one less amino acid than HuPrP in the region immediately upstream from the replacement.

Artificial PrP Genes

The real power of the present invention lies in the understanding that a variety of different artificial PrP genes can be created which, when inserted into a host animal, will render that animal susceptible to infection with prions which normally only infect a second and genetically diverse test animal. There are nearly an infinite number of possible artificial PrP genes which would meet the basic criteria of the invention, i.e. rendering a mammal such as a mouse susceptible to infection with prions which normally infect only a genetically diverse test animal such as a human. The MHu2M gene of the invention is only one specific example of an artificial gene which achieves the primary object of the invention. By reviewing FIGS. 3, 4 and 5 of U.S. Pat. No. 5,565,186 numerous other artificial gene possibilities will be deduced by those skilled in the art. Specifically, referring to FIG. 3 of U.S. Pat. No. 5,565,186 one can readily determine the amino acid sequence of mouse PrP and observe the positions wherein the mouse PrP sequence differs with a human PrP sequence. Thus, to create an artificial gene one can substitute a codon (or sequence of codons) of a mouse PrP gene with a codon (or sequence of codons) of a human PrP gene at the same position which will encode a different amino acid—any (but not all) of the codons where different sequences appear can be used for substitution. It will be understood by those skilled in the art that, if all of the codons where differences appear between the mouse and the human were substituted, the resulting gene would be the human PrP gene, which is not part of the present invention. However, as explained above, the entire human PrP gene can be inserted into a host animal such as a mouse to create a transgenic animal of the invention, expressing two fold or higher levels of human PrP$^C$ are included. Transgenic mice expressing only low levels of human PrP$^C$ are unlikely to become ill after inoculation with human prions. However, if the level of human PrP$^C$ expression is elevated, the transgenic animals become susceptible to infection with human prions. This is another means of overcoming the species barrier by what is referred to as a stochastic process.

Referring to FIG. 4 of U.S. Pat. No. 5,565,186 it can be seen how it would be possible to produce artificial PrP genes wherein the resulting gene could be inserted into a mouse in order to render the mouse susceptible to infection with bovine prions. A similar strategy with respect to producing a mouse which would be susceptible to infection with sheep prions can be deduced from reviewing FIG. 5 of U.S. Pat. No. 5,565,186. In addition to these possibilities those skilled in the art will recognize that, in certain instances, completely artificial nucleotide sequences can be used as corresponding substitutes for a portion of the natural sequence in order to obtain a useful artificial gene which, when inserted into an animal, will render that animal susceptible to infection with prions which normally would infect only a genetically diverse mammal.

Other artificial genes of the invention include genes which may be native or artificial and are operatively fused to an enhanced promoter such as a neuron specific enolase promoter. The enhanced promoter is such that when inserted into the host mammal will express the PrP gene at a level sufficiently high to render the host animal susceptible to infection with prions which normally only infect a genetically diverse test animal.

Evidence of Disease $PrP^{Sc}$ has been found in the brains of affected Tg(MHu2M) mice after inoculation with Hu(CJD) or Mo(RML) prions. Brain homogenates of Tg(MHu2M) were either left undigested or digested with proteinase K (BMB) at a final concentration of 20 $\mu$g/ml for 1 hour at 37° C. (even numbered lanes). Samples were resolved by SDSPAGE and then analyzed by Western blot.

The distribution of $PrP^C$ and $PrP^{Sc}$ in clinically sick Tg(MHu2M) mice inoculated with Mo(RML) and Hu(CJD) prions were detected by the histoblot method. The histoblots included those of coronal sections through the region of the hippocampus and thalamus. Differences are observed between: (A) $PrP^C$ in Mo(RML) infected mouse; (B) $PrP^C$ in sporadic CJD RG-infected mouse; (C) $PrP^{Sc}$ in Mo(RML) infected mouse; (D) $PrP^{Sc}$ in sporadic CJD RG-infected mouse; (E) $PrP^{Sc}$ in sporadic CJD EC-infected mouse; and (F) $PrP^{Sc}$ in iatrogenic CJD (#364)-infected mouse.

EXAMPLES

The following examples are put forth so as to provide those of ordinary skill in the art with a complete disclosure and description of how to make and use the chimeric genes, transgenic mice and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Chimeric Gene (MHu2M)

The source of the HuPrP ORF for construction of a n expression cassette has been described [Hsiao et al., *Nature* 338:342–345 (1989)]. The construction of the MHu2M gene is described in connection with the description of FIG. 1. All PrP ORF cassettes were flanked by SalI and XhoI, which cleave immediately adjacent to the PrP initiation and termination codons of the PrP ORF respectively, allowing for convenient subcloning into the cos.SHaTet cosmid expression vector [Scott et al., *Cell* 73:979–988 (1993)]. The isolation and screening of recombinant cosmid clones was achieved by methods which have been previously described [Scott et al., *Cell* 73:979–988 (1993)].

Example 2

Producing Transgenic Mice/Tg(MHu2M)

The nucleotide sequences of the HuPrP and MHu2MPrP ORFs of Example 1 were verified. The cosmid NotI fragments, recovered from large-scale DNA preparations, were used for microinjection into the pronuclei of fertilized C57BL/6×SJL or FVB/N oocytes as previously described [Scott et al., *Cell* 59:847–857 (1989); Scott et al., *Protein Sci*. 1:986–997 (1992)]. Genomic DNA isolated from tail tissue of weaning animals was screened for the presence of incorporated transgenes using a probe that hybridizes to the 3'-untranslated region of the SHaPrP gene contained in the cosSHa.Tet vector [Scott et al., *Protein Sci*. 1:986–997 (1992)]. The offspring obtained were tested and it was confirmed that the chimeric MHu2M gene was in tegrated into the genome of these offspring. As shown in Example 5 below, these mice were found to be susceptible to infection with human prions 100% of the time.

Example 3

Preparation of Brain Homogenates

A 10% [w/v] homogenate of a sample of thawed human brain tissue wa s prepared in phosphate buffered saline lacking calcium and magnesium ions. The tissue was initially dissociated using a sterile disposable homogenizer, and this suspension was subjected to repeated extrusion through an 18 gauge syringe needle followed by a 22 gauge needle. Samples for inoculation into test animals were diluted 10-fold. Homogenates of clinically sick Tg and non-Tg mouse brains were prepared in the same way except for the omission of the initial dissociation step.

Example 4

Sources of Prion Inocula

Human inocula were derived from frozen brain tissues of patients in which the clinical diagnosis of CJD or GSS had been confirmed by histopathological examination of brain tissues and, in most cases, by prion protein analysis. In some cases, the PrP gene was amplified by PCR of DNA isolated from patient blood and the PrP sequence determined by DNA sequence analysis. No HuPrP mutations were detect ed in cases of sporadic or iatrogenic CJD. The RML isolate was obtained from Swiss mice [Chandler, R. L., *Lancet* 1:1378–1379 (1961)] from a closed colony at the Rocky Mountain Laboratory or in Swiss CD-1 mice obtained from Charles River Laboratories.

Example 5

Determination of Scrapie Incubation Periods

Transgenic mice as per Example 2 were inoculated intracerebrally with 30 $\mu$l of brain extract using a 27 gauge needle inserted into the right parietal lobe. The preparation of inocula and criteria for diagnosis of scrapie in mice have been described [Carlson et al., Cell 46:503–511 (1986)]. Beginning 50 days after inoculation, the mice were examined for neurologic dysfunction every 3 days. When clinical signs of scrapie appeared, the mice were examined daily. When some animals whose death was obviously imminent were identified, their brains were taken for histopathologic studies (as per the procedures of Example 3) and confirmation of the diagnosis of scrapie.

Example 6

Immunoblot Analysis

For the determination of the relative levels of PrP expression in Tg mouse and human brains, protein concentrations were determined by bicinchoninic acid assay and immuno dots blots as previously described [Scott et al., Cell 73:979–988 (1993)]. Samples for Western blot analysis were prepared and western blots were performed as described previously [Towbin et al., Proc. Natl. Acad. Sci. USA 76:4350–4354 (1979)], except that an enhanced chemiluminescent (ECL) detection method (Amersham) was used. The blot was exposed to X-ray film for 5–60 seconds. α-PrP RO73 rabbit antiserum was used at a final dilution of 1:5000 and 3F4 monoclonal antibody was also employed [Serban et al., Neurology 40:110–117 (1990)].

Example 7

Tg(MHu2MPrP) Mice Are Susceptible to Human Prions

Using information from a systematic study of chimeric SHa/Mo PrP genes, a chimeric Hu/Mo PrP gene analogous to MH2M was constructed as per Example 1. This gene, which we call MHu2M, differs from MoPrP at 9 positions, all of which lie between codons 94 and 188 as is shown in FIG. 2. A Tg mouse was constructed expressing the MHu2M PrP gene and the founder designated Tg(MHu2M)FVB-B5378 as per Example 2. By serial dilution of Tg(MHu2M) mouse and human brain homogenates, we estimate that the level of MHu2MPrP$^C$ in the brains of these Tg(MHu2M) FVB-B5378 mice are similar to those of HuPrP$^C$ found in human brain using an immuno dot blotting procedure.

Tg(MHu2M) mice as per Example 2 were inoculated with brain homogenates from three unrelated Caucasian patients who had died of CJD. Two of the three patients died of sporadic CJD: one (R.G.) was a 56-year-old American female; the other (E.C.) was a 61-year-old Canadian female. In both cases, cerebrocortical biopsy showed severe spongiform degeneration. The third (#364) was a British youth who had contracted iatrogenic CJD after treatment for hypopituitarism with human growth hormone (HGH) derived from cadaveric pituitaries [Collinge et al., Lancet 337:1441–1442 (1991)]. Brain homogenates from all three CJD patients exhibited protease-resistant PrP by Western immunoblotting. This protease-resistant isoform of PrP is designated PrP$^{Sc}$, or often PrP$^{CJD}$ when it is found in humans.

All of the Tg(MHu2M) mice inoculated with homogenates from the CJD patients described above developed signs of central nervous system (CNS) dysfunction ~200 days after inoculation (see Table 1 below). The clinical signs were similar to those of murine scrapie. After developing clinical signs, the inoculated Tg(MHu2M) mice died rapidly, often within a day. Two of the eight uninoculated Tg(MHu2M) mice are now >500 days of age and remain well; the youngest of the other six uninoculated animals is older than the age at which inoculated Tg(MHu2M) mice developed signs of CNS dysfunction.

Inoculation of Tg(MHu2M) mice with Mo(RML) prions passaged in mice produced disease in 178±3 days, which is ~40 longer than Mo(RML) prions in non-Tg mice. Prolongation of incubation times in mice expressing non-murine transgenes is well established, and occurs presumably because the foreign PrP$^C$ molecule inhibits the conversion of MoPrP$^C$ into MoPrP$^{Sc}$ [Prusiner et al., Cell 63:673–686 (1990)]. In contrast to Tg(MHu2M) mice, incubation times for RML prions in Tg(MH2M) mice were the same as those of the non-Tg mice [Scott et al., Cell 73:979–988 (1993)].

TABLE 1

Incubation of human (CJD) and mouse (RML) prion inocula in Tg(MHu2M)FVB-B5378 mice

| Source | Inoculum | No.[a] | Range (days) | Incubation Times (mean days ± SE) Illness | Death[b] |
|---|---|---|---|---|---|
| Sporadic CJD | RG | 8/8 | 225–249 | 238 ± 3.2 | 240 ± 5.4(3) |
| Sporadic CJD | EC | 7/7 | 202–229 | 218 ± 4.6 | N.D. |
| Iatrogenic CJD | #364 | 9/9 | 221–245 | 232 ± 2.9 | 235 ± 3.9(5) |
| Mo | RML | 19/19 | 155–195 | 178 ± 3.3 | 203 ± 2.0(14) |

[a]Number of animals developing clinical sickness (neurological dysfunction) divided by the total number of animals inoculated. In the case of inoculum RG, three animals were found dead after 224, 238, and 243 days before a clinical diagnosis could be made. In the case of inoculum EC, two animals were found dead after 225 and 226 days before a clinical diagnosis could be made. In each case, these animals died at the same time thatclinical diagnosis was made in other inoculated animals.
[b]The number of mice dying of scrapie is shown in parentheses. Mice sacrificed for pathological examination are excluded from these calculations.

Example 8

Comparative Example

Tg(HuPrP) Mice Are Resistant to Human Prions

Tg mice expressing HuPrP were produced using the HuPrP gene ORF, which had been cloned into the cosSHa.Tet expression vector [Scott et al., Protein Sci. 1:986–997 (1992)]. Microinjection of outbred C57B6/SJL and inbred FVB mouse embryos resulted in two founder transgenic animals designated Tg(HuPrP)B6SJL-110 and Tg(HuPrP) FVB-152. We estimated by serial dilution of brain homogenates and immuno dot blotting, that the level of PrP$^C$ in the brains of the progeny of these founders express HuPrP at levels 4- to 8-fold higher than the level of HuPrP found in the human brain.

To determine whether expression of HuPrP in Tg(HuPrP) B6SJL-110 and Tg(HuPrP)FVB-152 conferred susceptibility to human prions, incubation periods were measured after inoculation of Tg(HuPrP) and non-Tg mice with brain extracts from 18 patients that had died of sporadic CJD, iatrogenic CJD, familial CJD or GSS. From experiments performed over the past 2.5 years, we concluded that the two lines of Tg(HuPrP) mice were no more responsive than non-Tg mice to human prions (see Table 2 below). The rate of transmission to Tg(HuPrP) mice was 8.3% (14 clinically sick mice out of 169 mice) which was similar to a transmission rate of 10.3% in control non-Tg mice (6 clinically sick mice out of 58 mice). In the infrequent event of a positive transmission, incubation times were extremely long ranging, from 590 days to 840 days in both Tg(HuPrP) and non-Tg mice. By this late time, many animals had died of intercurrent illnesses which complicated diagnosis. The difficulty of interpreting transmissions occurring after extremely long incubation periods is compounded by the heightened potential for artifactual results due to low levels of contaminating prions.

Statistical analysis shows that the frequency of Hu prion transmission to Tg(MHu2MPrP) mice compared to Tg(HuPrP) and non-Tg mice is highly significant using the Fisher's exact test, $p<10^{-7}$ [Mehta et al., *J. Am. Stat. Assn.* 78:(392) 427–434 (1983)]. When Hu prion transmission to Tg(HuPrP) mice was compared to non-Tg mice, the frequencies were similar, p=0.79.

To confirm the clinical diagnosis of prion disease, 5 ill Tg(HuPrP) and 1 non-Tg mice were sacrificed and brain extracts were examined for the presence of $PrP^{Sc}$ by Western blotting with the α-PrP antibodies, 3F4 mAb and RO73 antiserum [Kascsak et al., *J. Virol.* 61:3688–3693 (1987); Serban et al., *Neurology* 40:110–117 (1990)]. The 3F4 mAb reacts specifically with HuPrP allowing discrimination from MoPrP. $MoPrP^{Sc}$ was detected in the brain of the non-Tg mouse inoculated with sporadic CJD inoculum #87011 which developed clinical signs after 756 days, while 3F4-reactive $PrP^{Sc}$ was detected in the brains of two Tg(HuPrP) mice which developed clinical signs after 589 days post-inoculation with iatrogenic CJD inoculum #170. The equivalent transmission rates of human prions in Tg(HuPrP) and non-Tg mice indicate that this is a rare event with the same frequency of occurrence as the stochastic conversion of $MoPrP^C$ to $MoPrP^{Sc}$ induced by human prions.

The absence of either RO73- or 3F4-reactive $PrP^{Sc}$ in the brains of 3 out of the 6 mice analyzed may reflect the difficulty of accurately diagnosing prion disease in elderly animals. Some of the mice inherited prion diseases of both humans and Tg mice exhibit little or undetectable levels of protease-resistant PrP; yet, based on transmission studies, their brains contain prions and they show clear spongiform degeneration [Medori et al., *N. Engl. J. Med.* 326:444–449 (1992)].

In contrast to Tg(MHu2M) mice, Hu prions from patient RG have not transmitted to either Tg(HuPrP) or non-Tg mice after >330 days (see Table 2 below). Attempts to transmit preparations enriched for Hu prion rods prepared from the brain of patient RG have likewise been negative for >300 days. In addition, inoculum from the iatrogenic CJD case (#364) has produced illness in neither Tg(HuPrP) nor non-Tg mice after >780 days (as shown in Table 2 below).

TABLE 2

Incubation times in Tg(HuPrP)FVB-152 and Tg(HuPrP)B6SJL-110 mice after inoculation with brain extracts from patients with human prion diseases

| Host | Inoculum | $(n/_a n_o)$ | Incubation times (days ± SE)[b] |
|---|---|---|---|
| Tg152 | Sporadic CJD(#87011) | 1/10 | 706 |
| Non-Tg | Sporadic CJD(#87011) | 3/5 | 697.3 ± 51 |
| Tg 152 | Sporadic CJD(#88037) | 3/10 | 680 ± 28 |
| Tg 152 | Sporadic CJD(RG) | 0/10 | |
| Non-Tg | Sporadic CJD(RG) | 0/10 | |
| Tg 152 | Sporadic (RG) Rods | 0/8 | |
| Non-Tg | Sporadic (RG) Rods | 0/8 | |
| Tg 152 | Codon 102 GSS(#87027) | 4/10 | 724 ± 16 |
| Non-Tg | Codon 102 GSS(#87027) | 0/10 | 679 |
| Tg 152 | Codon 102 GSS(#87031) | 0/10 | |
| Non-Tg | Codon 102 GSS(#87031) | 1/5 | 742 |
| Tg 152 | Codon 178 F-CJD | 0/8 | |
| Non-Tg | Codon 178 F-CJD | 0/8 | |
| Tg 110 | Sporadic CJD(#87036) | 0/8 | |
| Non-Tg | Sporadic CJD(#87036) | 1/5 | 838 |
| Tg 110 | Iatrogenic CJD(#703) | 0/10 | |
| Non-Tg | Iatrogenic CJD(#703) | 0/5 | |
| Tg 110 | Iatrogenic CJD(#170) | 2/10 | 589 ± 0 |
| Non-Tg | Iatrogenic CJD(#170) | 0/5 | |
| Tg 110 | Iatrogenic CJD(#364) | 0/10 | |
| Non-Tg | Iatrogenic CJD(#364) | 0/5 | |
| Tg 110 | Codon 200 F-CJD | 1/8 | 791 |
| Tg 110 | Codon 217 GSS | 1/8 | 874 |
| Tg 110 | Codon 102 GSS-A | 0/10 | |
| Tg 110 | Codon 102 GSS-B | 1/8 | 694 |
| Tg 110 | Codon 117 GSS | 0/8 | |

[a]Number of animals developing clinical sickness divided by the total number of animals inoculated.
[b]Refers to time to diagnosis of illness.
Patients from which inoculum were derived are described in the following publications: [Collinge et al., Lancet 337:1441–1442 (1991); Hsiao et al., Nature 338:342–345 (1989); Hsiao et al., Neurology 41:681–684 (1991)].

Example 9

Formation of $MHu2MPrP^{Sc}$ or $MoPrP^{Sc}$ In the Brains of Tg(MHu2M) Mice

Some clinically sick Tg(MHu2M) mice inoculated with each of the three CJD prion inocula or RML prions were sacrificed for histopathological verification of disease and for prion protein analysis. Western blots of brain homogenates from Tg(MHu2M) mice infected with Hu prions probed with RO73 and 3F4 α-PrP antibodies revealed the presence of protease-resistant $PrP^{Sc}$ which reacted with the 3F4 monoclonal antibody showing this protease-resistant product to be MHu2M $PrP^{Sc}$. The epitope recognized by this antibody consists of a pair of methionine residues at positions 109 and 112 in PrP [Rogers et al., *J. Immunol.*

147:3568–3574 (1991)] which are contained in MHU2M but not in MoPrP as can be seen by the mouse/human comparison of FIG. 2. The polyclonal rabbit α-PrP antiserum RO73 diluted 1:5000 was poorly reactive with MHu2MPrP$^{Sc}$ as well as HuPrP$^C$ and HuPrP$^{Sc}$ from diseased human brains. Brain homogenates from Tg(MHu2M) mice infected with RML prions contained PrP$^{Sc}$ which was detectable only with RO73 and not 3F4 α-PrP antibodies, indicating that Tg(MHu2M) mice are capable of producing MoPrP$^{Sc}$ but not MHu2MPrP$^{Sc}$ in response to RML prions previously passaged in mice. While these findings are similar to those reported for Tg(SHaPrP) mice [Scott et al., Cell 59:847–857 (1989)], they contrast with those found for Tg(MH2MPrP) mice where MH2MPrP$^{Sc}$ was formed in response to RML prions [Scott et al., Cell 73:979–988 (1993)].

Example 10

Regional Distribution of PrP$^{Sc}$ and Patterns of Neuropathology

The distribution of Mo and MHu2M PrP$^C$ and PrP$^{Sc}$ is shown in histoblots of coronal brain sections through the hippocampus and thalamus of Tg(MHu2M) mice inoculated with RML or CJD prions. The weak immunoreactivity of MHu2M PrP with RO73 permitted a degree of analysis which had not been previously possible in Tg mice expressing SHaPrP or MH2MPrP because these PrP$^{Sc}$ species react with this antibody. The pattern of PrP$^{Sc}$ deposition was highly dependent upon the species of origin of the infectious prions. When inoculated with RML prions, histoblots of the brains of Tg(MHu2M) were similar to those of CD-1 mice infected with RML prions, revealing a diffuse pattern of MoPrP$^{Sc}$ deposition in the hippocampus, thalamus, hypothalamus and all layers of the neocortex. The histoblot pattern of was strikingly different for Tg(MHu2M) mice inoculated with CJD prions. The deposition of MHu2MPrP$^{Sc}$ was confined primarily to the deep layers of the neocortex, the thalamus, particularly the ventral posterior medial thalamic nucleus, the hypothalamus and the putamen. The hippocampal region and the outer layers of the neocortex were spared. Interestingly, while the hippocampus was completely devoid of MHu2MPrP$^{Sc}$, this region showed the most intense MHu2MPrP$^C$ signal. The same pattern of MHu2MPrP$^{Sc}$ deposition was consistently observed in histoblots of Tg(MHu2M) mice inoculated with all three CJD prion isolates prepared from human brain. It is noteworthy that the pattern of MHu2MPrP$^{Sc}$ deposition is similar to the pattern of PrP$^{CJD}$ deposition observed in histoblots of the brain from which inoculum RG was derived [Taraboulos et al., Proc. Natl. Acad. Sci. USA 89:7620–7624 (1992)]. The spongiform degeneration in the brains of Tg(MHu2M) mice infected with Mo(RML) and Hu(CJD) prions reflected the patterns of PrP$^{Sc}$ accumulation described above.

Experimental Protocols

Numerous additional examples of transgenic and hybrid mice as well as comparative examples and methods of testing such are described below. These examples and methods are listed in Tables 3–7. With respect to such the (1) methods of making mice; (2) brain homogenates; (3) prion inocula; (4) measurement of incubation times; (5) immunoblotting; and (6) immunohistochemistry are described below.

Production Of Transgenic Mice

The MoPrP-A sequence used was derived from Swiss CD-1 mice Locht, C., et al., "Molecular closing and complete sequence of prior protein cDNA from mouse brain infected with the scrapie agent," Proc. Natl. Acad. Sci. USA 83:6372–6376 (1986). Construction of the MoPrP ORF cassette has been previously described Rogers, M., Serban, D., Gyuris, T., Scott, M., Torchia, T., and Prusiner, S. B. (1991). Epitope mapping of the Syrian hamster prior protein utilizing chimeric and mutant genes in a vaccinia virus expressions system. J. Immunol. 147:3568–3574. The construction of the MoPrP-P101L expression cassette containing a substitution of a leucine for proline codon at residue 101 of the mouse PrP gene, corresponding to the GSS mutation at codon 102 of the human PrP gene has ben described Hsiao, K. and Prusiner, S. B. (1990). Inherited human prion diseases. Neuroloqy 40:1820–1827. ORF cassettes were digested with Bglll (which cleaves immediately adjacent to the initiation codon). The 5' protruding termini were filled in using Klenow, and Sall linkers were added. Recombinant clones were cleaved with Sall and Xhol (which cleaves immediately past the PrP termination codon), and purified ORF fragments were ligated to the Sall-cut cosSHa.Tet cosmid expression vector Scott, M. R., Köhler, R., Foster, D., and Prusiner, S. B. (1992). Chimeric prion protein expression in cultured cells and transgenic mice. Protein Sci. 1:986–997. The isolation of recombinant cosmid clones was achieved by methods that have been previously described Scott, M., Groth D., Foster, D., Torchia, M., Yang, S.-L., DeArmond, S. J., and Prusiner, S. B. (1993). Propagation of prions with artificial properties in transgenic mice expressing chimeric PrP genes. Cell 73:979–988. Notl fragments, recovered from large-scale DNA cosmid preparations, were used for microinjection into the pronuclei of fertilized FVB/N oocytes as previously described Scott, M., Foster, D., Mirenda, C., Serban D., Coufal, F., Wälchli, M., Growth, D., Carlson, G., DeArmond, S. J., Westaway, D., and Prusiner, S. B. (1989). Transgenic mice expressing hamster prion protein produce species-specific infectivity and amyloid plaques. Cell 59:847–857. Genomic DNA isolated from tail tissue of weaning animals was screened for the presence of incorporated transgenes using a probe that hybridizes to the 3'-untranslated region of the SHaPrP gene contained in the cosDHa.Tet vector Scott, M. R., Köhler, R., Foster, D., and Prusiner, S. B. (1992).

Preparation of Brain Homogenates

Ten % [w/v] homogenates of mouse brain were prepared by repeated extrusion through an 18 gauge syringe needle followed by a 22 gauge needle in phosphate buffered saline (PBS) lacking calcium and magnesium ions. For immunoblot analysis, samples were cleared of cell debris by a brief low-speed centrifugation. Purified Hu prions were prepared using a protocol previously developed for SHa prions Prusiner et al., (1983) Scrapie Prions Aggregate to Form Amyloid-like Birefringent Rods. Cell 35, 349–358.

Prion Inocula

Human brain specimens were collected from patients dying of sporadic, inherited or infectious prion disease. The iatrogenic CJD denoted 364 was provided by Dr. John Collinge. The RML isolate from Swiss mice Chandler, R. L., "Encephalopathy in mice produced by inoculation with scrapie brain material," Lancet 1:1378–1379 (1961) was provided by Dr. William Hadlow and was passaged in Swiss mice CD-1 mice obtained from charles River Laboratories (Wilmington, Mass.). For transmission of neurodegeneration from spontaneously ill Tg (MoPrP-P101L) mice, brain homogenates were prepared.

Measurement Of Incubation Times

Mice were inoculated intracerebrally with 30 μl of samples prepared from brain using 27 gauge needle inserted into the right parietal lobe, and observed for signs of disease. Samples were diluted 10-fold in PBS prior to inoculation. Additionally, uninoculated Tg(MoPrP-P101L0 and Tg(MoPrP-A) mice were observed for spontaneous CNS disease. The preparation of inocula and criteria for diagnosis of scrapie in mice have been described Carlson, G. A., et al., "Linage of prion protein and scrapie incubation time genes," *Cell* 46:503–511 (1986). When clinical signs of CNS dysfunction appeared, the mice were examined daily. To confirm the clinical diagnosis, the brains of some animals whose deaths were obviously imminent were taken for histopathological studies.

Immunoblotting

Total protein concentrations in brain homogenates were determined by bicinchoninic acid assay. Immuno dot blots for the determination of the relative levels of PrP expression in Tg mouse brains were performed as previously described (Scott et al., 1993). Samples for Western blot analyses were prepared by digesting brain homogenates with 20 μg proteinase K for 60 min at 37° C. Western blots were performed as described previously Barry, R. A., et al., "Monoclonal antibodies to the cellular and scrapie prion proteins,"*J. Infect. Dis.*, 154:518–521 (1986); Towbin, H., et al., "Electrophoretic transfer of proteins from polyacrylamide gels to nitrocellulose sheets: Procedure and some applications," *Proc. Natl. Acad. Sci. USA* 76:4350–4354 (1979), except that an enhanced chemiluminescent (ECL) detection method (Amersham, Arlington Heights, Ill.) was used. The lot was exposed to X-ray film α-PrP RO73 rabbit antiserum was used at a final dilution of 1,5000.

Immunohistochemistry

For immunohistochemistry, endogenous peroxidase activity was blocked with methanol-hydrogen peroxide (2 ml of 30% $H_2O_2$ in 200 ml methanol). To enhance PrP immunoreactivity, the sections were immersed in 1.3 mM HCl and autoclaved at 121° C. for 10 min Muramoto et al., (1992) The sequential development of abnormal prion protein accumulation in mice with Creuzfeldt-Jakob disease. *Am. J. Pathol.* 140, 1411–1420. When temperature decreased, the slides were placed under running tap water for 10 min followed by rinsing with TB (50 mM Tris-HCl, pH 7.6, with 150 mM NaCl). Nonspecific protein binding was blocked with TBS (25 mM Tris-HCl, pH 7.8; 0.05% Tween 20; 0.5M NaCl; and 5% nonfat milk) for 10 min. The α-PrP polyclonal rabbit RO73 antiserum wa diluted 1:250 in TBS. Tissue sections were incubated with the primary antiserum overnight at 4° C. Following 2 rinses with TB containing 0.1% Triton-X and once in TB, the sections were incubated with biotinylates goat anti-rabbit lgG (Vector Laboratories, Burlingame, Calif.) in TBS, 1:100 dilution for 30 min at room temperature. After 2 rinses with TB containing 0.1% Triton-X, the sections were incubated with an avidin-biotin-peroxidase complex (Vector Laboratories) for 30 min at room temperature. Three rinses in TB were then followed by a 3–5 min reaction with diaminobenzadine solution (5 mg diaminobenzadine tetrahydrochloride, 68 mg imidazole, and 7 mg $NaN_3$ in 10 ml of TB), to which 100 μl of 0.0015% $H_2O_2$ was added.

Peroxidase immunohistochemistry with antibodies to glial fibrillary acidic protein was used to evaluate the extent of reactive astrocytic gliosis. Hydeolytic autoclaving was used to detect PrP immunoreactivity (Muramoto et al., 1992).

Examples Re Tables 3–7

Transgenic Mice With Human and Chimeric PrP Genes

FVB mice expressing human, chimeric Hu/Mo and mutant PrP genes were constructed using the cos.SHaTet cosmid expression vector derived from the Syrian hamster (SHa) (Scott et al., 1992). Table 3 below shows the designation of the mouse line, the expressed $PrP^C$ molecules and the approximate level of transgenic expression. Also indicated are those mouse lines that were crossed with $Prnp^{0/0}$ mice in which the mouse PrP gene had been disrupted by homologous recombination (Büeler et al., 1992). Backcrossing these mice produced animals in those encoded by the transgene. While SV129ES cells were used to generate a chimeric mouse with a disrupted PrP allele, that mouse was mated with a C57BL mouse and the offspring crossed to each other to produce null animals. Subsequently, these $Prnp^{0/0}$ mice were repeatedly crossed onto the FVB background.

TABLE 3

Nomenclature and Characteristics of Transgenic Mouse Lines

| Mouse Line Description | Expressed $PrP^c$ Molecules | PrP Transgene Expression | Sequence[b] |
|---|---|---|---|
| (i) Tg(HuPrP) mice | | | |
| Tg(HuPrP) 152/FVB | Hu,Mo | ~4-8x | V129 |
| Tg(HuPrp) 152/Prbp$^{0/0}$ | Hu | ~4-8x | V129 |
| Tg(HuPrP) 440/Prnp$^{0/0}$ | Hu | ~2x | M129 |
| (ii) Tg(MHu2M) mice | | | |
| Tg(MHu2M) 5378/FVB | MHu2M, Mo | ~1x | M128 |
| Tg(MHu2M) 5378/Prnp$^{0/0}$ | MHu2M | ~1x | M128 |
| Tg(MHu2M-P101L)69/Prnp$^{0/0}$ | MHu2M-L | ~2x | M128, L10 |

Since the Hu prion inocula are brain homogenates or purified prion rods from a variety of patients who died of prion disease, the designations for the patients as well as clinical phenotypes are listed in Table 4 below. The PrP genotypes of the patients are also described.

TABLE 4

Brain Inocula From Patients Who Died of Prion Disease

Sporadic Inocula and Infectious CJD prions Containing wt $PrP^{Sc}$

| Human Inoculum | Prion Disease | Genotype of $PrP^d$ |
|---|---|---|
| PG | sporadic CJD | wt, M/M129 |
| EC | sporadic CJD | wt, M/M129 |
| MA | sporadic CJD | wt, M/M129 |
| PO | sporadic CJD | wt, M/M129 |
| PC | sporadic CJD | wt, M/M129 |
| 364 | iatrogenic CJD | wt, M/M129 |

GSS and Familial CJD prions containing mutant $PrP^{Sc}$

| JJ | GSS | P102L, V/V128 |
|---|---|---|
| LJ-1 | familial CJD | E200K, M/M129 |
| CA | familial CJD | E200K, M/M129 |
| FH | familial CJD | E200K, V/M129 |

[a]Substitution of L for P codon 102 in HuPrP or at codon 101 in MoPrP or chimeric MHu2MPrP is denoted as "-L".
[b]Level of PrP transgene expression in brain was measured by serial dilution of the samples followed by dot immunoblotting. Each sample was compared to $PrP^C$ in non-Tg mouse or human brain.
[c]Amino acid residues at codon 129 or codon 101.
[d]Patients with sporadic or iatrogenic CJD had wild-type (wt) PrP ORFs. The PrP alleles encode either M or V at position as noted. Mutations in the PrP gene are denoted by the wt amino acid followed by the codon number and the mutant residue.

MoPrP$^C$ Inhibits Propagation of Human Prions in Tg(HuPrP) Mice

When Tg(HuPrP)152/FVB mice and non-Tg littermates were inoculated with Hu prions from sporadic or iatrogenic CJD as well as inherited prion disease cases, ~10% of each group of mice developed CNS dysfunction (Telling et al., 1994). Some of the ill mice produced MoPrP$^{Sc}$ and others HuPrP$^{Sc}$ based on Western immunoblots developed with polyclonal α-PrP antiserum that reacts with both Hu and MoPrP and with α-PrP monoclonal antibodies (mAb) that react with Hu but not MoPrP. Those mice that produced HuPrP$^{Sc}$ demonstrated that HuPrP$^{Sc}$ could be formed in Mo cells but the process was too infrequent for further study. After Crossing the Tg(HuPrP) 152/FVB Mice onto the Prnp$^{0/0}$ Background, They became Susceptible to Hu Prions (Table 5)

When Tg(HuPrp)152/FVB mice were inoculated with Hu prions from a case of sporadic CJD, referred to as RG, only one Tg mouse out of a group of 10 developed neurologic symptoms at >720 d, while non-Tg littermates responded similarly with one. animal out of a group of 10 inoculate mice developing neurologic symptoms at >700 d.

TABLE 5

Transmission Of Hu Prions to Tg(HuPrP)/Prnp$^{0/0}$ mice

| Recipient Mouse Line | Inoculum$^a$ | Incubation Time mean d ± SEM (n/no) |
|---|---|---|
| (A) Tg(HuPrP)FVB mice | | |
| Tg(HuPrP)152/FVB | sCJD(RG) | 721 ± 0 (1/10)$^b$ |
| Non-Tg 152/FVB | sCJD(RG) | 701 ± 0 (1/10)$^b$ |
| Tg(HuPrP)152/FVB | sCJD(RG, purified rods) | 677 ± 0 (1/10) |
| Non-Tg 152/FVB | sCJD(RG, purified rods) | 643 ± 42 (3/10) |
| (B) Tg(HuPrP)Prnp$^{0/0}$ mice | | |
| Tg(HuPrp)152/Prnp$^{0/0}$ | sCJD(RG) | 263 ± 2 (6/6) |
| Tg(HuPrP)152/Prnp$^{0/0}$ | sCJD(EC) | 254 ± 6 (9/9) |
| Tg(HuPrP)152/Prnp$^{0/0}$ | iCJD(364) | 262 ± 8 (5/5) |
| Tg(HuPrP)440/Prnp$^{0/0}$ | iCJD(364) | 164 ± 2 (7/7) |

$^a$All samples were 10% (w/w) brain homogenates unless otherwise noted that were diluted 1:10 prior to inoculation. sCJD is sporadic CJD and iCJD is iatrogenic CJD. Patients initials referring to inocula in Table 1B are given in parenthesis.
$^b$Transmissions previously reported (Telling et al., 1994).

Similar rates of transmission were observed when Tg(HuPrP)152/FVB and non-Tg mice were inoculated with a preparation highly enriched for PrP$^{Sc}$ prepared from the brain of RG (see Section B of Table 5). Using the α-PrP 3F4 monoclonal antibody (mAb) Kascsak, R. J., et al., "Mouse polyclonal and monoclonal antibody to scrapie-associated fibril proteins," J. Virol. 61:3688–3693 (1987), we estimated, by serial dilution and dot immunoblotting of brain homogenates which were normalized for protein concentration, the level of HuPrP$^C$ in brains of the Tg(HuPrP)152/FVB mice to be ~4–8 fold higher than HuPrP$^C$ in human brain (Table 3).

Since earlier studies had shown that heterologous PrP$^C$ inhibited the conversion of PrP$^{Sc}$ as manifest by prolongation of the incubation time Büeler, H., et al., "Mice devoid of PrP are resistant to scrapie," Cell 73:1339–1347 (1993); Prusiner, S. B., et al., "Immunologic and molecular biological studies of prion proteins in bovine spongiform encephalopathy," J. Infect. Dis. 167:602–613 (1993); Prusiner, S. B., et al., "Transgenetic studies implicate interactions between homologous PrP isoforms in scrapie prion replication," Cell 63:673–686 (1990), we removed MoPrP$^C$ by producing Tg(HuPRP)152/Prnp$^{0/0}$ mice. When Tg(HuPRP)152/Prnp$^{0/0}$ were inoculated with Hu prions, they developed signs of neurologic dysfunction with incubation times between 260 and 300 d (Table 5 shown in Section B).

MoPrP Gene Ablation In Mice Expressing Chimeric PrP

Crossing the transgene array from the already susceptible Tg(MHu2M)5378/FVB mice onto the Prnp$^{0/0}$ background resulted in a decrease (~20%) in CJD incubation times (Table 6 Sections A and B). Using the α-PrP 3F4 mAb, we estimated the level of MHu2MPrP$^C$ in the brains of the Tg(MHu2m)5378/FVB mice to be slightly less than HuPrP$^C$ in human brain.

TABLE 6

Transmission of Hu prions to Tg(MHu2MPrP)mice

| Inoculum$^a$ | Incubation Time mean d ± SEM (n/no) |
|---|---|
| (A) Tg(MHu2M)/FVB mice inoculated with sporadic or infectious CJD | |
| sCJD(RG) | 238 ± 3 (8/8)$^b$ |
| sCJD(EC) | 218 ± 5 (7/7)$^b$ |
| iCJD(364) | 232 ± 3 (9/9)$^b$ |
| iCJD(364)$^c$ | 231 ± 6 (9/9) |
| sCJD(MA) | 222 ± 1 (4/4) |
| (B) Tg(MHu2M)/Prnp$^{0/0}$ mice inoculated with sporadic or infectious CJD | |
| sCJD(RC) | 202 ± 2 (6/10) |
| sCJD(RG) | 191 ± 3 (10/10) |
| iCJD(364) | 192 ± 6 (8/9) |
| iCJD(364)$^c$ | 190 ± 6 (8/8) |
| sCJD(MA) | 180 ± 5 (8/8) |
| sCJD(RO) | 217 ± 2 (9/9) |
| (C) Tg(MHu2M)/Prnp$^{0/0}$ mice inoculated with inherited GSS or CJD | |
| GSS(JJ,P102L) | >280 (0/10) |
| fCJD(LJ1,E200K) | 170 ± 2 (10/10) |
| fCJD(CA,E200K) | 180 ± 9 (9/9) |
| fCJD(FH,E200K) | >250 (0/7) |

$^a$All samples were 10% (w/v) brain homogenates unless otherwise noted that were diluted 1:10 prior to inoculation. sCJD is sporadic CJD, iCJD is iatrogenic CJD, GSS is Gerstmann-Straussler-Scheinker disease with the codon 102 mutation and fCJD is familial CJD with the codon 200 mutation. Patients initials referring to inocula in Table 4 are given in parenthesis. If the PrP gene of the patient carried a mutation, then the mutation is noted after the patients initials.
$^b$Transmissions previously reported (Telling et al., 1994).
$^c$This is a second inoculum prepared from a different brain region of iatrogenic CJD patient 364.

Any comparison between the incubation times of Tg(HuPrP)152/Prnp$^{0/0}$ and Tg(MHu2M)5378/Prnp$^{0/0}$ mice must take into account the different levels of transgene expression. Generally, the level of transgene expression is inversely related to the length of the incubation time. Although the incubation times are similar for Tg(HuPrP) 152/Prnp$^{0/0}$ and Tg(MHu2M)5378/Prnp$^{0/0}$ mice inoculated with Hu prions (Tables 5 and 6 Section B of each), the Tg(HuPrP)152/Prnp$^{0/0}$ express 5–10-fold more of the transgene product than Tg(MHu2M)5378/Prnp$^{0/0}$ mice. This suggests that the chimeric transgene or some modified version may be superior to HuPrP in terms of generating mice with the shortest incubation times for bioassays of Hu prions.

Transmission of Chimeric Prions

Species specific amino acid variations in PrP are known to contribute significantly to the "species barrier" Prusiner, S. B., et al., "Transgenetic studies implicate interactions between homologous PrP isoforms in scrapie prion replication," *Cell* 63:673–686 (1990); Scott, M., Foster, D., Mirenda, C., Serban D., Coufal, F., Wälchli, M., Growth, D., Carlson, G., DeArmond, S. J., Westaway, D., and Prusiner, S. B. (1989). Transgenic mice expressing hamster prion protein produce species-specific infectivity and amyloid plagues. *Cell* 59:847–857. Prolongation of incubation times on primary passage of prions between species is generally seen while second passage in the same species results in a shortening and stabilization of incubation times Pattison, I. H., "Experiments with scrapie with special reference to the nature of the agent and the pathology of the disease," *Slow, Latent and Temperate Virus Infections*, NINDB Monograph 2, D. C. Gajdusek, et al., eds. (Washington, D.C.: U.S. Government Printing), pp. 249–257 (1965). Primary passage of Hu prions from a sporadic CJD case (EC) produced CNS disease in Tg(MHu2M)5378/FVB with an incubation time of 218±5 d(±SEM) (Table 6 Section A). Brains from ill mice were collected and homogenates inoculated into mice from the same Tg line. Passage of these chimeric prions in Tg(MHu2M)5378/FVB mice gave incubation times similar to those seen with Hu prions on the primary passage (Table 7 Section A). This finding shows that these Tg(MHu2M) 5378/FVB mice are completely permissive for Hu prions. Passage of chimeric prions in Tg(MHu2M)5378/Prnp$^{0/0}$ mice resulted in a shortening of the incubation time by ~20% presumably due to the elimination of MoPrP$^C$; i.e., ablating the endogenous mouse prion protein gene.

TABLE 7

Serial transmission of chimeric Hu/Mo prions in Tg(MHu2M) mice

| Recipient Mouse Line | Inoculum[a] | Illness | Incubation Times mean d ± SEM (n/no) Death |
|---|---|---|---|
| (A) Chimeric prions produced in Tg(MHu2M) mice inoculated with CJD prions | | | |
| Tg(MHu2M)5378/FVB | MHu2M(sCJD)[b] | 220 ± 3 (7/7)[c] | 226 ± 1(5) |
| Non-Tg5378/FVB | MHu2M(sCJD)[b] | >340 | |
| Tg(MHu2M)5378/FVB | MHu2M(sCJD)[d] | 226 ± 3 (9/9) | 228 ± 1(6) |
| Non-Tg5378/FVB | MHu2M(sCJD)[d] | >340 | |
| Tg(MHu2M)5378/ Prnp$^{0/0}$ | MHu2M(sCJD)[d] | 189 ± 4 (8/8) | 192 ± 1(4) |
| Tg(MHu2M)5378/ Prnp$^{0/0}$ | MHu2M(sCJD)[d] | 183 ± 5 (7/7) | 190 ± 3(4) |
| (B) Mouse prions produced in Tg(MHu2M) or non-Tg mice inoculated with RML prions | | | |
| Tg(MHu2M)5378/FVB | Mo(RML) | 178 ± 3 (19/19) | 203 ± 2 (14)[e] |
| NonTg5378/FVB | Mo(RML) | 127 ± 2 (18/18) | 156 ± 2(5) |
| Tg(MHu2M)5378/FVB | MHu2M(RML)[f] | 185 ± 1 (7/7) | 211 ± 1(3) |
| Tg(MHu2M)5378/FVB | MHu2M(RML)[g] | 189 ± 2 (7/7) | 211 ± 9(3) |
| Non-Tg5378/FVB | MHu2M(RML)[g] | 134 ± 3 (5/5) | N.D. |
| Tg(MHu2M)5378/ Prnp$^{0/0}$ | Mo(RML) | >340 | |
| Tg(MHu2M)5378/ Prnp$^{0/0}$ | MHu2M(RML)[f] | >300 | |
| Tg(MHu2M)5378/ Prnp$^{0/0}$ | MHu2M(RML)[g] | >300 | |

[a]Notation in parentheses indicate inoculum used in initial passage in Tg(MHu2M) mice.
[b]Mice were inoculated with chimeric prions generated in the brain of a Tg(MHu2M)5378/FVB mouse that had been inoculated with a brain homogenate prepared from patient EC who died of sporadic CJD.
[c]Number of mice developing CNS illness divided by the number inoculated are given in parentheses.
[d]Mice were inoculated with chimeric prions generated in the brain of a second Tg(MHu2M)5378/FVB mouse that had been inoculated with a brain homogenate prepared from patient EC who died of sporadic CJD.
[e]Data from (Telling et al. 1994).
[f]Mice were inoculated with Mo prions generated in the brain of a Tg(MHu2M)5378/FVB mouse that had been inoculated with RML Mo prions.
[g]Mice were inoculated with Mo prions generated in the brain of a second Tg(MHu2M)5378/FVB mouse that had been inoculated with RML Mo prions.

Specificity of Chimeric Prions and Transgenes

Non-Tg5378/FVB littermates, which express only MoPrP$^C$, inoculated with the chimeric prions have remained well for >340 days. Thus it appears that homology between the substrate PrP$^C$ and the product PrP$^{Sc}$ in the region bounded by residues 96 to 167 is essential for prion propagation. Conversely, Tg(MHu2M)Prnp$^{0/0}$ mice are resistant to Mo prions; they have remained well for >340 days after inoculation (Table 7 Section B).

Although Tg(MHu2M)5378/FVB mice are permissive for Mo(RML) prions, the incubation time of 178±3 d(±SEM) was protracted compared to that of 127±2 d(±SEM) for non-Tg5378/FVB littermates (Table 7 Section B). Two homogenates derived from Tg(MHu2M)5378/FVB mice were inoculated with Mo(RML) prions were passaged in Tg(MHu2M)5378/FVB mice and non-Tg littermates. The incubation time in the Tg(MHu2M)5378/FVB mice did not change while the incubation time in the non-Tg mice shortened to the incubation time registered for primary passage of Mo(RML) prions in these mice (Table 7 Section B). This behavior and the fact that MoPrP$^{Sc}$ is made in response to inoculation with Mo prions (Telling et al., 1994) appears to show that Tg(MHu2M)5378/FVB mice propagate Mo prions from endogenous MoPrP$^C$ and not from MHu2MPrP$^C$.
Residue 129 Mismatches between PrP$^{Sc}$ in the Inoculum and Transgene-encoded PrP$^C$ In Caucasians (Palmer et al., 1991) but not Asians Tateishi and Kitamoto, (1993) Developments in diagnosis for prion diseases. *Br. Med. Bull.* 49,971–979 homozygosity for M or V codon 129 has been reported to predispose people to development of sporadic CJD. Homozygosity at codon 129 in some Baker et al., (1991) Amino acid polymorphism in human prion protein and age at death in inherited prion disease. *Lancet* 337, 1286; Goldfarb, L. G., et al., "The molecular genetics of human transmissible spongiform encephalopathy", *Prion Diseases of Humans and Animals*, S. B. Prusiner et al., eds. (London: Ellis Horwood), pp. 139–153 (1992) but not other inherited prion diseases diminished the age of onset of CNS dysfunction; Gabizon et al., (1993) Mutation and polymorphism of the prion protein gene in Libyan Jews with Creutzfelt-Jakob disease. *Am. J. Hum. Genet* 33, 828–835. The Tg(HuPrP)152 mice express HuPrP with V at codon 129 while another line Tg(HyPrP) 440 synthesizes HuPrP with M at 129. When Tg(HuPrP) 152/Prnp$^{0/0}$ and Tg(HuPrP)440/Prnp$^{0/0}$ mice were inoculated with prions from iatrogenic and sporadic cases, the shortest incubation times occurred when the amino acid residues at position 129 were the same in PrP$^C$ and ioculated PrP$^{Sc}$. Tg(HuPrP)440/Prnp$^{0/0}$ mice inoculated with a case of iatrogenic CJD from a patient with a M/M codon 129 haplotype, referred to as 364, exhibited a mean incubation time of 164±2 d(±SEM) while the same inoculum produced disease in Tg(HuPrP)152/Prnp$^{0/0}$ mice with a mean incubation time of 253±6 d (±SEM). Two cases of sporadic CJD derived from patients with the M/M codon 129 haplotype, referred to as EC and RG, produced disease in Tg(HuPrP) 152/Prnp$^{0/0}$ mice with mean incubation times of 254±2 d (±SEM), respectively (Table 5 Section B).
Tg(MHu2M-P101L) Mice Expressing the GSS Mutation To produce a model of GSS, we created lines of mice carrying the P102L point mutation in both the MoPrP and HuPrP g enes. The Tg(MoPrP-P101L)87 and 174 mice expressing the mutant PrP$^C$ at high levels developed disease spontaneously between 50 and 300 d of age (Hsiao et al., 1994; Hsiao et al., 1990). In contrast, a line designated Tg(HuPrP-P102L)/FVB was observed for >700 d and unlike the Tg(MoPrP-P101L) mice, did not develop spontaneous neurologic disease.

The successful transmission of Hu prions to Tg(MHu2M) 5378/FVB mice promoted us to produce Tg(MHu2M-P101L)69/Prnp$^{0/0}$ mice. Unlike the Tg(HuPrP-P102L) mice, these Tg(MHu2M-P101L) mice spontaneously developed neurologic disease. The mean age of illness in Tg(MHu2M-P1201L) mice was 362±13 d (±SEM). By 480 days, ~90% of Tg(MHu2M-P1201L) mice developed CNS dysfunction (n/n$_o$=15/17). An intense reactive astrocytic gliosis was found in the gray matter of all mice expressing the MHu2M-P101L transgene at the time they exhibited signs of CNS dysfunction. Modest spongiform degeneration and PrP immunoreactivity were found in the white matter of all mice examined. Besides the Tg(HuPrP-P102)7/FVB mice, additional controls include Tg(HuPrP)/FVB, Tg(MHu2M)/FVB and Tg(MHu2M)/Prnp$^{0/0}$ mice, none of which have developed CNS degeneration spontaneously.

Transmission of GSS Human Prions to Tg(MHu2M-P101L) Mice

Although Tg(MHu2M-P101L)69Prnp$^{0/0}$ mice eventually develop a spontaneous neurologic disorder, we attempted to determine whether the illness would appear more rapidly if the animals are inoculated. Both wt and GSS Hu prions were inoculated. Tg(MHu2M-P101L)69Prnp$^{0/0}$ mice were inoculated at about 70 days of age with brain extract from a GSS patient referred to as JJ, who carried the P102L mutation, or with brain extracts from two sporadic CJD cases (RG and EC in Table 5). These mice inoculated with prions from the GSS patient JJ died after 171±2.8 d (±SEM). The man age of 247±3 d (±SEM) at which these Tg mice became ill was more than 100 days earlier than the age at which uninoculated controls developed signs of CNS dysfunction. Although the Tg(MHu2M-P101) mice inoculated with prions from the sporadic CJD cases have a mean incubation time of 259±10 d (±SEM) (n/n$_o$=12/15), these mice were 350±11 d (±SEM) of age at the time of death. The age of these mice prevented us from concluding whether they became ill from the inoculated prions or spontaneously as a result of the MHu2MPrP-P102L mutant protein.

Our findings demonstrate that Hu prions from the GSS patient carrying the point mutation homologous to that in the transgene caused disease more rapidly than did wt Hu prions from sporadic cases of CJD. Conversely, the Hu prions from the GSS patient have failed to produce disease >280 d after inoculation in Tg(MHu2M)5376/Prnp$^{0/0}$ mice (Table 6 Section C); whereas, Hu prions containing wt PrP$^{Sc}$ cause disease in Tg(MHu2M)5378/Prnp$^{0/0}$ mice at ~190 d (Table 6 Section B). The onset of illness in the GSS inoculated mice was relatively synchronous, with a range of 30 d while the onset was less uniform in the spontaneously ill and CJD-inoculated Tg(MHu2M-P101L)69/Prnp$^{0/0}$ mice with ranges of 210 d and 157 d, respectively.

Tg(MHu2M-P101L) mice inoculated with GSS prions exhibited spongiform degeneration and reactive astrocytic gliosis similar to uninoculated Tg(MHu2M-P101L) mice that developed CNS dysfunction spontaneously. However, the inoculated mice showed more neuronal loss and more intense and widespread GFAP immunostaining than uninoculated, spontaneously ill mice. PrP accumulation was more intense in some gray matter regions such as the hippocampus in the Tg(MHu2M-P101L) mice inoculated with GSS prions than the uninoculated animals exhibiting spontaneous illness.

Uninoculated Tg(MHu2M-P101L)69/Prnp$^{0/0}$ mice that developed spontaneously did not have any detectable protease-resistant PrP (PrP 27–30) on Western blots. This finding is similar to that reported previously with Tg(MoPrp-P101L)87 and 174 mice that also develops CNS illness spontaneously Hsiao, K. K., Groth, D., Scott, M., Yang, S.-L., Serban, H., Rapp, D., Foster, D., Torchia, M., DeArmond S. J., and Prusiner, S. B. (1994). Serial transmission in rodents of neurologic disease from transgenic mice expressing mutant prion protein. Likewise, the brain of the GSS patient JJ from which the inoculum was derived contained relatively little or no detectable PrP 27–30 even though numerous PrP amyloid plaques were found Hsiao, K., Baker, H. F., Crow, T. J., Poulter, M., Owen, F., Terwilliger, J. D., Westaway, D., Ott, J., and Prusiner, S. B. (1989). Linkage of a prion protein missense variant to Gerstmann-Sträussler syndrome. *Nature* 338:342–345. On some occasions, a weak, diffuse band comigrating with PrP 27–30 has been observed with homogenates prepared from the brain of patient JJ. Whether regional variations in protease-resistant PrP are responsible for these inconsistent results remains to be established. In addition, no PrP 27–30 was found in the brains of the Tg(MHu2M-P101L)69/Prnp$^{0/0}$ mice inoculated with homogenate prepared from the brain of the GSS patient JJ at the time they were sacrificed after development of CNS dysfunction. The relatively short incubation times in the Tg(MHu2M-P101L)69/Prnp$^{0/0}$ mice argue that the brain of JJ contained high prion titers even if PrP 27–30 was difficult to detect. From these results, we conclude that PrP$^{Sc}$ containing the P102L mutation is probably less protease-resistant than wtPrP or PrP carrying other mutations.

Transmission of Familial CJD (E200K) Human Prions to Tg(MHu2M) Mice

Brain extracts were prepared from two patients who carried the E200K mutation and died of CJD (Gabizon et al., 1993). The extracts were inoculated into Tg(MHu2M)5378/Prnp$^{0/0}$ mice that developed CNS dysfunction in 170±2 d (±SEM, n=10) for the LJ1 case and ~160 d for the CA case. In contrast to the P102L mutation, Hu prions from patients who carried the E200K mutation caused disease as rapidly in Tg(MHu2M)5378/Prnp$^{0/0}$ mice as Hu prions containing wtPrP$^{Sc}$ from sporadic CJD cases (Table 6 Section C).

Transgenics—Alternative Methods of Producing

Transgenic mice expressing moderate to high levels of wild-type human prion (HuPrP) were originally constructed by microinjecting fertilized FVB embryos with cosmid DNA expressing human PrP. The results of a large number of transmission experiments with sporadic, iatrogenic and familial prion cases revealed that these mice were no more responsive to human prions than their non-transgenic counterparts. We have demonstrated that by eliminating endogenous mouse (Mo)PrP expression in these transgenic mice, transmission of human prions becomes efficient with mean incubation times as low as 160 days. Expression of even half the normal amount of mouse PrP was sufficient to inhibit human prion propagation. These results demonstrate that Mo PrP is extremely inhibitory for the propagation of human prions in transgenic mice even though the level of expression of HuPrP was approximately 8 to 16-fold higher than Mo PrP. These and the results of other genetic experiments have led to the notion that a third component, which we refer to as protein X, must feature in prion propagation. Evidence points to the C-terminal region of PrP as the location for the protein X binding site.

The results of these experiments demonstrate that current transgenic mouse models for the assay of human prions can be improved upon substantially. Because of the inhibitory effects of MoPrP in mice expressing heterologous transgenes, eliminating its expression is crucial for the efficient propagation of heterologous transgenes, eliminating its expressing is crucial for the efficient propagation of heterologous prions in these transgenic mice. This can be achieved in one of several ways.

Homologous Recombination—Producing Transgenic Mice Crossed with MoPrP Gene Ablated Mice FVB mice expressing human PrP genes have been constructed using the cos.SHaTet cosmid expression vector derived from the Syrian hamster (SHa). The FVB strain of mice contain and express the normal complement of MoPrP genes and so one method for introducing the HuPrP transgene array into a background in which MoPrP expression is ablated is by genetic crosses between the transgenic FVB-derived line and a second line of transgenic mice in which both MoPrP genes were disrupted. Mice homozygous for the disrupted Prnp genes were created. These genetically-altered mice were created by a process known as homologous recombination (Thomas and Capecchi, Cell 51:503–512, 1987) in which a selectable disrupted MoPrP gene was introduced into embryonic stem (ES) cells from SV129 mice. Blastocysts of C57BL/6J mice were injected with SV129 ES cells in which one copy of the MoPrP gene had been disrupted thus generating a chimeric mouse with one disrupted allele. That mouse was mated with a C57BL mouse and the offspring crossed to each other to produce null animals in which both copies of the MoPrP gene were disrupted, referred to as $Prnp^{0/0}$ mice. Subsequently, these $Prnp^{0/0}$ mice were repeatedly crossed onto the FVB background. FVB-derived transgenic mouse lines Tg(HuPrP) FVB/152 and Tg(HuPrP)FVB/440 were crossed with $Prnp^{0/0}$ mice. Backcrossing these mice produced animals in which the only $PrP^C$ molecules that were synthesized were those encoded by the transgene.

Producing Transgenic Mice Using Fertilized Oocytes From MoPrP Gene Ablated Mice

The second method for producing transgenic mice in which the only $PrP^C$ molecules synthesized are encoded by the HuPrP transgene is by directly microinjecting DNA from a vector capable of directing expression of HuPrP. Derivatives of the cos.SHaTet cosmid expression vector containing the HuPrP open reading frame were used—(other expression systems could be used including a cosmid consisting of the cognate HuPrP gene or other vectors capable of appropriate expression of HuPrP in transgenic mice). Using embryos from the originally created C57BL-derived $Prnp^{0/0}$ mice we encountered great difficulty in producing transgenic mice by this method because of the poor survival rates of microinjected embryos. These $Prnp^{0/0}$ mice were subsequently repeatedly crossed onto the FVB background to produce mice which were genetically ~95% FVB but which were also homozygous for the gene ablation. By modifying the $Prnp^{0/0}$ mice in this way we now have very high rates of production of transgenic mice by this method.

Gene Replacement

A different approach to eliminating the inhibitory effects of MoPrP would be to create new lines of transgenic mice in which the endogenous MoPrP genes were replaced with HuPrP genes by homologous recombination in ES cells. This gene-replacement approach (Hasty et al., Nature 350:243–6, 1991; Valancius and Smithies, Mol. Cell Biol. 11:1402–8, 1991) is a variation of the geneinsertion experiment described above in which $Prnp^{0/0}$ mice were created. In gene replacement, the sequences in the input DNA completely replace those in the target DNA. The methodologies that are currently available permit gene targeting at high efficiency and fidelity so that it should in theory be possible to replace the MoPrP gene with the homologous HuPrP gene in ES stem cells and thereby produce mice that are homozygous for this replacement.

After completing gene replacement with either HuPrP of chimeric MHu2MPrP, these mice are mated to transgenic mice expressing high levels of the homologous protein such as HuPrP or MHu2MPrP. The mice will express the highest levels of the foreign PrP of interest and possess the shortest incubation times. For example, mice with ~50 copies of the MoPrP transgene have incubation times of ~60 days after inoculation with ~106 $ID_{50}$ units if the endogenous MoPrP genes are ablated; in contrast, incubation times of ~48 days were found if the endogenous MoPrP genes are left intact (Table 8). Alternatively, the fertilized eggs from these mice with gene replacements can be microinjected with the DNA encoding either the same PrP gene as that replaced or a related gene.

Creating Mammals which Express Protein X

Identifying the amino acid sequence(s) in MoPrP responsible for the binding of mouse protein X and construct a modified MoPrP gene in which the sequence for this binding site is mutated. Such a benign MoPrP molecule will not interfere with human prion propagation in transgenic mice expressing HuPrP because protein X is not sequestered by the mutant MoPrP. Following the above-described procedures in which the MoPrP gene is replaced with HuPrP or modified MoPrP genes, it is possible to create transgenic mice expressing HuPrP using these new genetic backgrounds either by genetic crosses or by direct microinjection of a vector capable of directing expression of HuPrP into fertilized embryos from these newly-created transgenic mouse lines.

Use of Multiple Promoters to Increase the Level of PrP Gene Expression

Further modifications of the current transgenic mouse models for the assay of human prions involve the production of transgenic mice expressing HuPrP under the control of promoter/enhancer sequences from genes other than PrP which normally express their gene products in the central nervous system (CNS). Examples of such promoters include neuron specific enolase (NSE) (Farlie et al., Natl. Acad. Sti USA 92:4397–4401, 1995) or platelet-derived growth factor (PDGF) (Sasahara et al., Cell 64:217–227, 1991). Expression of HuPrP under these circumstances will result in levels of expression much higher than normally achieved by PrP promoter/enhancer sequences leading to greatly shortened human prion incubation times in transgenic mice expressing these constructs. Alternatively, by creating several lines of transgenic mice in which HuPrP expression is directed by a variety of different gene constructs and then mating these mice to produce lines in which HuPrP was expressed simultaneously in a variety of different cell types in the CNS, lines of mice may be created in which HuPrP expression levels are extremely high and incubation times are exceedingly short.

Mice Expressing Multiple PrP Different Transgenes to Increase the Range of Prions to which they are Susceptible Create lines of transgenic mice simultaneously expressing several different forms of HuPrP derived from patients with polymorphisms and/or with mutations at particular amino acid residues of HuPrP. We have recently discovered that human prion propagation, at least in the case of the polymorphism at codon 129 and the GSS mutation at codon 102, occurs most efficiently when the amino acid sequences at these residues are matched in $PrP^{Sc}$ in the inoculum and $PrP^C$ encoded by the transgene. By creating a line in which a number of different forms of HuPrP are expressed, prions with a variety of different polymorphisms and/or mutations are transmitted efficiently to the same host.

TABLE 8

Prion incubation times in Tg(MoPrP-A) mice

| Recipient Mouse | Inoculum[a] | Illness[b] | Incubation Times mean d ± SEM (n/no) Death[c] |
|---|---|---|---|
| (A) Tg(PrP-A) mice | | | |
| Tg(MoPrP-A)4053 | None | 710 ± 37 (4/20) | N.D. |
| Tg(MoPrP-A)4053 | RML | 48 ± 1 (21/21) | 53 ± 2 (12) |
| Tg(MoPrP-A)4053 | Tg4053-2 (RML) | 48 ± 2 (10/10) | 58 ± 2 (7) |
| Non-Tg 4053 | RML | 127 ± 2 (18/18) | 156 ± 2 (5) |
| Tg(MoPrP-A)4053/ Prnp$^{0/0}$ | RML | 59 ± 2 (9/9) | 65 ± 2 (6) |
| (B) Swiss CD-1 mice | | | |
| Swiss CD-1[c] | RML | 138 ± 1 (24/24) | 159 ± 3 (24) |
| Swiss CD-1 | Tg4053-1 (RML) | 140 ± 3 (10/10) | 163 ± 2 (6) |
| Swiss CD-1 | Tg4053-2 (RML) | 138 ± 5 (9/9) | 169 ± 2 (6) |

[a]Notation in parentheses indicate inoculum used in initial passage. Single digit following a hyphen distinguishes individual mice from a particular line.
[b]The number of mice developing clinical signs of scrapie is shown in parentheses.
[c]The number of mice dying of scrapie is shown in parentheses. Mice that were sacrificed for pathologic examination were excluded from these calculations.
[d]Data from Butler, et al., J. Vrol. 62:1558–1584, 1988.

The instant invention is shown and described herein in what is considered to be a most practical and preferred embodiments. It is recognized, however, that departures may be made from which are within the scope of the invention and that modifications will occur to one who is skilled in the art upon reading this disclosure.

We claim:

1. A method of making a standardized prion preparation, comprising:

producing a plurality of transgenic mice each having an ablated endogenous PrP gene and an exogenous PrP gene wherein the mice are susceptible to infection with a prion which generally only infects a genetically diverse mammal, and further wherein the mice exhibit symptoms of prion disease within 200 days or less after inoculation with a prion which generally only infects a genetically diverse mammal;

inoculating the mice with a composition comprising prions from a genetically diverse mammal;

observing the mice until the mice exhibit symptoms of prion infection;

harvesting brain tissue from the mice exhibiting symptoms of prion infection; and homogenizing the harvested brain tissue from said plurality of mice to provide a stantdardized prion preparation.

2. The method of claim 1, wherein the exogenous PrP gene comprises a mouse PrP gene sequence with one or more, but not all, of its codons which differ from a PrP gene of the genetically diverse mammal replaced with a corresponding codon of the PrP gene of the genetically diverse mammal.

3. The method of claim 2, wherein both alleles of the endogenous mouse PrP gene are ablated and further where an exogenous PrP gene is operably inserted in their genome.

4. The method of claim 3, wherein the exogenous PrP gene comprises a nucleotide sequence corresponding to that of an endogenous PrP gene of a genetically diverse mammal selected from the group consisting of a human, cow, sheep, horse, chicken, cat or dog.

5. The method of claim 1 wherein the genetically diverse mammal is a human.

6. The method of claim 1, wherein the genetically diverse mammal is a cow.

7. The method of claim 1, wherein 50 or more transgenic mice are produced.

* * * * *